United States Patent
Hill et al.

(10) Patent No.: US 10,945,961 B2
(45) Date of Patent: Mar. 16, 2021

(54) METHOD USING ENTERIC-COATED ETIDRONATE FOR TREATING CALCIFICATION, HYPERCALCAEMIA, AND CALCINOSIS OF THE BRAIN AND OTHER ORGANS

(71) Applicants: Bryan Alan Hill, Edison, NJ (US); John Stephan McCarty, Lyndonville, VT (US); Jeffrey Arlin Loeb, Chicago, IL (US)

(72) Inventors: Bryan Alan Hill, Edison, NJ (US); John Stephan McCarty, Lyndonville, VT (US); Jeffrey Arlin Loeb, Chicago, IL (US)

(73) Assignee: ZY YTHERAPEUTICS LLC, Mendham, NJ (US)

( * ) Notice: Subject to any disclaimer, the term of this patent is extended or adjusted under 35 U.S.C. 154(b) by 0 days.

(21) Appl. No.: 16/106,346

(22) Filed: Aug. 21, 2018

(65) Prior Publication Data
US 2019/0054030 A1    Feb. 21, 2019

Related U.S. Application Data

(60) Provisional application No. 62/548,344, filed on Aug. 21, 2017.

(51) Int. Cl.
| | | |
|---|---|---|
| A61K 9/28 | (2006.01) |
| A61K 9/00 | (2006.01) |
| A61K 31/663 | (2006.01) |
| A61P 25/08 | (2006.01) |
| G16H 20/10 | (2018.01) |
| G16H 70/20 | (2018.01) |
| A61B 5/00 | (2006.01) |
| G16H 70/40 | (2018.01) |
| A61B 6/00 | (2006.01) |
| G06F 19/28 | (2011.01) |
| G16B 50/00 | (2019.01) |
| A61B 5/145 | (2006.01) |
| A61K 9/48 | (2006.01) |
| G16H 50/20 | (2018.01) |
| A61K 9/50 | (2006.01) |
| G16H 50/70 | (2018.01) |
| A61B 5/021 | (2006.01) |

(52) U.S. Cl.
CPC ........ *A61K 9/2846* (2013.01); *A61B 5/14546* (2013.01); *A61B 5/4839* (2013.01); *A61B 5/4848* (2013.01); *A61B 6/501* (2013.01); *A61K 9/0053* (2013.01); *A61K 9/0056* (2013.01); *A61K 9/4816* (2013.01); *A61K 9/4891* (2013.01); *A61K 9/5026* (2013.01); *A61K 31/663* (2013.01); *A61P 25/08* (2018.01); *G16B 50/00* (2019.02); *G16H 20/10* (2018.01); *G16H 50/20* (2018.01); *G16H 50/70* (2018.01); *G16H 70/20* (2018.01); *G16H 70/40* (2018.01); *A61B 5/002* (2013.01); *A61B 5/021* (2013.01)

(58) Field of Classification Search
CPC ...... A61K 9/2846; A61K 9/0053; A61P 25/08
See application file for complete search history.

(56) References Cited

U.S. PATENT DOCUMENTS 6,432,413 B1 * 8/2002 Loeb .................... A61K 31/663
424/400

OTHER PUBLICATIONS

Loeb et al., J. Neuro. Sci., (2006), v.243, p. 77-81.*
Pazianas et al., Therapeutics and Clinical Risk Management, (2013), 3(9), p. 395-402.*

* cited by examiner

*Primary Examiner* — Yong L Chu
(74) *Attorney, Agent, or Firm* — William Adrian Miles Mansfield

(57) ABSTRACT

Among other things, compositions, kits, and methods for epilepsy therapy using a process for treating calcinosis manifested in Neurocysticercosis, Tuberous Sclerosis Complex, and Sturge-Weber Syndrome; an automated platform for real-time diagnosis and treatment of calcinosis comprising a computer-implemented method for using predictive analytics for administering a novel drug, Kamini™, to human patients generated at least in part from information that has been accumulated automatically from on-line resources.

1 Claim, 9 Drawing Sheets ically effective close of at least one

METHOD USING ENTERIC-COATED ETIDRONATE FOR TREATING CALCIFICATION, HYPERCALCAEMIA, AND CALCINOSIS OF THE BRAIN AND OTHER ORGANS

CROSS-REFERENCE TO RELATED APPLICATION

This application claims the benefit of U.S. Provisional Patent Application No. 62/548,344, filed on Aug. 21, 2017, which is incorporated by reference herein in its entirety.

NOTICE OF COPYRIGHTS, TRADEMARKS, AND TRADE DRESS

A portion of the disclosure of this patent document contains material that is subject to copyright protection. This patent document may show and/or describe matter that is or may become trade dress of the owner(s). The copyright and trade dress owners have no objection to the facsimile reproduction by anyone of the patent disclosure as it appears in the Patent and Trademark Office patent files or records, but otherwise reserves all copyrights and trade dress rights whatsoever. Kamini™ is an enteric-coated disodium etidronate optimized by Zy Therapeutics, LLC for treating neurological calcifications and other disease-producing calcifications.

TECHNICAL FIELD

The present invention, fully described in the claims, relates generally to the application of drugs to treat diseases caused by calcinosis.

BACKGROUND

The pathologic over-supply of calcium in the body and brain has severe consequences leading to extreme morbidity and eventual mortality. Neurodegenerative disorders and their related syndromes (including epilepsy are a major detriment to the quality of life of millions of patients worldwide. Of particular note, are the rare and orphan variants of these diseases that, by definition, are greatly misunderstood and historically underfunded in terms of clinical drug development. Even though these diseases appear to be small in numbers when considering their underlying causes (genetics, infection), combining commonalities of disease progression, i.e., accumulation of metabolic wastes and other cellular breakdown materials allows us to see that the numbers of people suffering from these diseases is great and growing.

One such common breakdown pathway is the accumulation of calcium and calcium ions in the intracellular and extracellular spaces of damaged cells. Calcium is essential for normal cell physiology and, under normal circumstances, homeostatic mechanisms tightly regulate intracellular calcium. Accumulation of calcium in soft tissue is referred to as calcinosis. Calcinosis of the brain or physiological intracranial calcification occurs in about 0.3-1.5% of cases of epilepsy. It is generally asymptomatic and is detected incidentally by neuroimaging. Pathological basal ganglia calcification is due to various causes, including metabolic disorders and infectious and genetic diseases. Besides tetany and seizures this condition is presented by Parkinsonism and dementia. Such Parkinsonism does not respond to drugs containing levodopa. Infectious causes (Toxoplasmosis, Rubella, Cytomegalovirus, Cysticercosis, Neurocysticercosis, and AIDS) give multiple and asymmetric intracranial calcification. Inherited and neurodegenerative diseases cause symmetrical, bilateral basal ganglia calcification which is not related to metabolic disorders (blood calcium level and other), these include: Tuberous Sclerosis Complex, Sturge-Weber Syndrome, Fahr's Disease, Down syndrome and several others.

Three associated diseases indicative of calcinosis of the brain are currently without treatment or are treated unsuccessfully: Neurocysticercosis, Tuberous Sclerosis Complex, and Sturge-Weber Syndrome. All three disorders have distinct etiologies but commonly result in focal calcifications at the sites of the disease, with seizures and headaches being the most debilitating clinical manifestations.

SUMMARY OF THE INVENTION

In general, in an aspect, a method for treating a neurological condition in a human patient produced by calcinosis including diagnosing the condition by means of a real-time, interactive medical intelligence system, devising a drug regimen by means of a real-time, interactive, computer-implemented medical intelligence system, applying at least one safe and pharmaceutically effective close of at least one oral drug according to said drug regimen, monitoring dosage level and the realization of symptom relief, obtaining auxiliary medical information for effectiveness, revising said drug regimen to reduce side effects, adjusting said drug regimen to optimize symptom relief, and devising a long-term treatment drug regimen adjusted for optimized symptom relief.

Embodiments can include one or more of the following features: (1) use of an enteric-coated bisphosphonate, wherein the enteric-coated bisphosphonate is disodium etidronate; (2) a treatment method described in which the human patient is a pediatric patient and the enteric-coated disodium etidronate is formulated as chewable tablets or as a liquid which is targeted for extended release in the patient's proximal jejunum; (3) treatment for a human epilepsy patient comprising administering disodium etidronate at a dose of 2.5 to 20 mg/kg/day; (4) treatment using the active bisphosphonate, Kamini™, a formulation of disodium etidronate combined with sustained release technologies given at a dose of between 5 mg/kg/day to 15 mg/kg/day depending on the mass of the patient.

In general, in an aspect, sustained release technologies, configured to obtain direct placement of active pharmaceutical ingredient (disodium etidronate) into the proximal jejunum to ensure optimal absorption into the body, will include: 1) platform technologies: a) single and multi-layer tablets, in the preferred embodiment 200 mg and 400 mg versions; b) osmotic tablets; c) one or more tablets within tablets; d) liquid drug layering on pellets and functional coating; e) powder drug layering on pellets and functional coating; and f) extrusion spheronization and functional coating; or 2) delayed release technologies: a) enteric coating on tablets and on drug layered pellets for release in intestinal region; b) enteric coating on tablets and on drug layered pellets for release in colon region; or 3) sustained release technology: a) matrix tablet using polymers; b) zero order release using tablet; or c) barrier membrane coating on drug layered pellets; or 4) combination of release profile technology: a) immediate-release/sustained-release combination; b) pulsatile release; or 5) chewable tablet technology.

In general, in an aspect, a kit for treating a calcinosis-induced epilepsy in a human patient, the kit comprising: a drug composition comprising an enteric-coated bisphosphonate; instructions for use of the drug composition; and a delayed, release, enteric-coated tablet; and a non-transitory computer readable medium operable to store medical instructions to cause a computing system to provide medical guidance.

In general, in one aspect, an oral drug comprised of a safe and effective pharmaceutically active bisphosphonate, and, means for effecting delayed release of the bisphosphonate in the lower gastrointestinal tract to provide delivery of the pharmaceutical composition to the lower gastrointestinal tract of the human subject, specifically the proximal jejunum, and pharmaceutically effective absorption of the bisphosphonate, substantially alleviating upper gastrointestinal tract irritation and damage.

In an aspect, a drug composition for treating calcinosis-induced epilepsy, the composition comprising a bisphosphonate and a pH-mediated polymer designed to perforate and release at the optimal time so as to maximize absorption of the treatment via extended release.

Implementations of the computing system for medical guidance may include the following features: a predictive analytics module; a library of diagnostics models; and a treatment protocol database configured to operate on historical data and current observations of the patient configured to determine the optimal treatment for the calcinosis condition then issue instructions for producing and monitoring a drug regimen for treating calcinosis-based epilepsy wherein instructions, diagrams, and protocols are communicated to the medical personnel by means of a user device or display module.

In general, in another aspect, said kit is further operable to receive, from a radiological device, a neurological image characteristic of calcinosis for diagnosis of epilepsy caused by calcinosis and a computing system configured to issue instructions for producing and monitoring a drug regimen for treating calcinosis-based epilepsy.

In another aspect, a kit for treating epilepsy in a human patient, the kit comprising: (a) a non-transitory computer readable medium storing instructions for causing a computing system to receive from an radiological device, a neurological image characteristic of calcinosis for diagnosis of epilepsy caused by calcinosis; (b) a computing system configured to issue instructions for producing and monitoring a drug regimen for treating calcinosis-based epilepsy; (c) active and therapeutically applied bisphosphonate for treating calcinosis; (d) a composition of chelating bisphosphonate and a means for delayed release to form a safe and effective anti-calcinosis drug.

In one aspect, a medical blockchain configured to facilitate: 1) drug provenance—tracking of drugs to eliminate drug diversion and counterfeiting; and 2) use of the blockchain to perform due diligence in clinical and business development and licensing decisions: a) clinical outcome due diligence, b) scientific due diligence, c) business due diligence, and d) use of smart contracts for yes/no—go/no go decisions regarding treatment protocols; 2) valuation of individual projects and/or proofs of concept (tokenization); 3) trading of pre-IPO securities related to developmental ideas/concepts related to developmental ideas/proofs of concepts; 4) management of overall clinical drug development processes and timelines; 5) blockchain-based smart contract management of process, timelines, and milestones (i.e., smart contract that only pays out when a clinical trial site randomizes the pre-determined number of study subjects); 6) drug development milestones and GANNT/Go—No Go decision making process; 7) intellectual property/proportional ownership of intellectual property based on proof of work and amount of actual work performed on a given project (meritocracy); 8) blockchain-based management of clinical trial protocols; 9) blockchain-based clinical trial management: a) clinical trial data and comments from investigators/regulators; b) clinical trial outcomes reported directly by study patients; c) tracking of study drug/finished product (per new FDA guidance at https://www.accessdata.fda.gov/scripts/cdrh/cfdocs/cfcfr/CFRSearch.cfm?CFRPart=211&showFR=1&subpartNode=21:4.0.1.1.11.7).

In general, in one aspect, use of said method for treating the neurological condition produced by calcinosis in Neurocysticercosis.

In general, in one aspect, use of said method for treating the neurological condition produced by calcinosis in Tuber Sclerosis Complex.

In general, in one aspect, use of said method to treat the neurological condition produced by calcinosis in Sturge-Weber Syndrome.

Some or all of the above needs may be addressed by certain embodiments of the invention. The present invention, fully described in the claims, overcomes the limitations of conventional approaches by facilitating better compliance with medical regimens and addressing previously untreated conditions. Aspects and advantages of the invention will be set forth in part in the following description, or may be obvious from the description, or may be learned through practice of the invention.

These and other aspects, features, implementations, and advantages, and combinations of them, can be expressed as methods, apparatus, systems, components, program products, business methods, and means or steps for performing functions, or combinations of them.

Other features, aspects, implementations, and advantages will become apparent from the description, the drawings, and the claims.

BRIEF DESCRIPTION OF DISEASES TO BE TREATED

Neurocysticercosis and Calcification

Cysticercosis and neurocysticercosis are caused by taeniasis, an intestinal infection derived from ingesting adult tapeworms and/or their eggs. The most important: human Taenia tapeworm infections are caused by *Taenia solium* (pork tapeworm) and *T. saginata* (beef tapeworm). Humans become infected with *T. saginata* when they consume beef which has not been adequately cooked. Taeniasis due to *T. saginata* has no major impact on human health. Infection also occurs in humans when they eat raw or undercooked pork (*Taenia solium*). Humans can also become infected with *T. solium* eggs by ingesting contaminated food or water (human cysticercosis) or as a result of poor hygiene. Tapeworm larvae (cysticerci) develop in the muscles, skin, eyes and the central nervous system. When cysts develop in the brain, neurocysticercosis may result. Symptoms include epilepsy, severe headache and blindness, and, if left untreated, it can be fatal.

Neurocysticercosis is the most frequent preventable cause of epilepsy worldwide. Neurocysticercosis mainly affects the health and livelihoods of subsistence farming communities in developing countries of Africa, Asia, and Latin America. Due to global immigration, both the prevalence and incidence of Neurocysticercosis is growing. *T. solium* cysticercosis/neurocysticercosis remains a neglected disease, and was added by WHO to the list of major neglected tropical diseases in 2010. Neurocysticercosis is considered a rare and orphan disease in the United States.

Neurocysticercosis is associated with a variety of symptoms and signs depending on the number, size, stage and location of the pathological changes as well as the host's immune response and the parasite's genotype, but it can also be clinically asymptomatic. Symptoms may include chronic headaches, blindness, seizures (epilepsy if they are recurrent, intractable epilepsy if unresponsive to medication), hydrocephalus, meningitis, dementia and symptoms caused by lesions occupying spaces of the central nervous system.

Neurocysticercosis a Biological Model for Intracranial Calcification and Epileptogenesis Neurocysticercosis is the leading cause of epilepsy in the world. Thus, neurocysticercosis offers an excellent opportunity to study prospectively the natural history of the genesis of seizures and epilepsy in a human population. This is due to its unique epidemiology and timing of seizures associated with increased inflammation, a predictable occurrence of seizures in the treatment of parenchymal disease, and subsequent development of epilepsy commonly localized to calcified lesions. It is likely that information gained from studies of Neurocysticercosis will be applicable to other conditions in which inflammation plays a prominent causal role such as in brain trauma, infections, and strokes, since they likely share common pathways that culminate in seizure activity. The story of progression of Neurocysticercosis includes inflammation, calcification, immunoreaction, and cyclical and compounding brain damage (neurodegeneration). The present invention, fully described in the claims, addresses these issues and demonstrates that Kamini™ is a useful treatment for these conditions.

The present invention fully described in the claims, uses the disease progression of neurocysticercosis as a biological model for calcinosis-derived epilepsy. For this reason, it is important to delve deeper into the progression of the disease and the causes of calcinosis related to it. As previously stated, neurocysticercosis is a major cause of seizures and other neurologic problems in many less developed countries and a significant health concern in developed countries as well, mostly due to migration of infected persons. There are multiple ways that cysticercosis and Neurocysticercosis can cause seizures, mostly as direct or indirect effects of inflammation. For instance, seizures occur early in the disease in the setting of intense inflammation associated with viable or degenerating cysts. Treatment of the underlying infection and prevention of the ensuing calcinosis at this point is critical. Seizures can also occur later as a result of infarcts related to vasculitis and thrombosis of penetrating vessels from subarachnoid cysticercosis. Encephalomalacia and gliosis, end results of prior inflammation, have also been documented in neurocysticercosis and are other potential causes of seizure activity. Finally, a growing body of evidence suggests the more chronic cysticercal granuloma is associated with seizure activity either before or after calcification. Small, punctate, single or multiple calcifications are common in *T. solium* endemic populations and there is good evidence to indicate that most are calcified cysticercal granulomas.

Multiple or single punctate cerebral calcifications are infrequent in other infectious diseases and commonly distinguishable. Toxoplasmosis, cytomegalovirus, and rubella infections can cause cerebral calcifications after congenital infections but only those caused by toxoplasmosis can be easily confused with calcific cysticercosis. However, their presence early in life and associated clinical settings are distinctive. The patterns and nature of the calcifications in cytomegalovirus and rubella are different. Untreated cerebral tuberculosis lesions are not usually calcified although they tend to calcify after resolution, infrequently following therapy. In contrast, serial observations of treated and untreated patients with neurocysticercosis have documented the frequent evolution of cystic lesions to typical punctate calcifications. Biochemical and histologic studies of typical calcified lesions detected collagen characteristic of cysticerci and not host. Single enhancing lesions are well studied in India and these are mostly degenerating cysticerci that commonly calcify. Therefore, the presence of characteristic cerebral calcifications in the correct clinical setting is mostly chronic cerebral cysticercosis. Intracerebral calcifications are a common finding in persons with seizures or epilepsy in endemic populations and this finding suggests a role in the pathophysiology of seizures in these groups. Some of the differences among studies may be due to failure to differentiate patients experiencing acute symptomatic seizures in those with active (live or degenerating cysts) lesions from those with epilepsy. Although there is variability between studies, calcifications are common and can be the most frequent finding on brain imaging in certain populations, Prevalence ranges from 9% to 18% in randomized studies of endemic populations and up to 83% in selected populations with seizures. One of the more definitive studies found that calcifications alone were more frequent in those with seizures compared to those without seizures in a well-defined rural population. Typical calcifications were found in 36% and 35% of persons with seizures in two different villages compared to 15% and 9% in matched controls without a history of seizures. Cysts or degenerating cysts in this study were responsible for about 25% of the seizures in patients with cysticercosis. In an endemic village of Peru, 9 (31%) of 29 patients with epilepsy demonstrated lesions compatible with cysticercosis and 6 (20.7%) showed only calcifications. In contrast, only 15% of 38 without a history of seizures had lesions compatible with cysticercosis and all were calcifications (Cysticercosis Working Group in Peru 2003). Similarly, in a study of a prospectively evaluated rural Honduran population with neurocysticercosis and epilepsy, Medina et al. found that 76% had only calcifications, 9% cystic lesions, and 15% mixed lesions.

There are at least three pieces of evidence that suggest calcified lesions play a role in epileptogenesis: (1) high prevalence of typical cerebral calcifications in patients with seizures or epilepsy in the absence of other etiologies; (2) a positive correlation between endemic populations with increased proportions of calcification and seizure activity; and (3) an increased risk of continued seizure activity due to single cysticercal granuloma that calcify.

Calcifications can be foci of seizure activity. That some calcified lesions are able to initiate seizure activity comes from a correlation of the signs, symptoms, and abnormal EEGs with the neuroanatomic location of specific calcifications on imaging. Electroclinical activity correlates with the location of brain calcifications in 26% to 55% of the cases. As suggested by the authors of these studies, failure to localize seizure activity to more of the calcified lesions can be due to inherent limitations and constraints of the methodology, duration, or timing of the studies, spread of electrical activity from silent regions along anatomic pathways, or other lesions or processes as the cause of seizure activity. Perhaps the most direct evidence implicating calcified lesions as foci of seizure activity and other focal neurologic manifestations is the episodic appearance of perilesional edema often accompanied by corresponding clinical findings. Perilesional edema appears as a bright signal using MRI FLAIR or T2 imaging. It is almost always accompanied by enhancement around the calcified focus. This phenomenon is now well documented and has been noted by multiple investigators working in various geographic regions. Interestingly, in any given individual, one subset of calcifications may undergo recurrent episodes of perilesional edema, while another subset remains quiescent. As it is detectable on imaging, its occurrence, potential treatments, and prevention can easily be assessed. There is little known about the natural history, clinical importance, and pathophysiology of perilesional edema. From anecdotal reports, collected series, and previous observations in patients with seizures, perilesional edema related to calcifications appears to be relatively frequent, ranging from 23% to about 35% in patients with calcified neurocysticercosis and a history of seizures. Associated symptoms range from frequent and disabling manifestations that usually consist of seizures or focal neurologic disease to no outward clinical manifestations. The pathophysiology of perilesional edema is unknown. Calcified granulomas are a result of the host's inflammatory response to viable or degenerating cystic larva, so one hypothesis is that there are episodic host inflammatory responses to residual antigen that is intermittently released or recognized by the host similarly to the responses provoked by anticysticidal drugs. One perplexing aspect of the phenomenon is that only certain. calcified foci are capable of developing perilesional edema, so only lesions that undergo perilesional edema would be predicted to contain or expose antigen while others would not. In support of this idea a recent report correlated the presence of a recognizable scolex in specific calcified lesions with the presence of perilesional edema. The presence of a scolex (the head-like part of tapeworm, bearing hooks and suckers by which the attached to the tissues of its host) is indicative of the presence of recognizable parasite remnants and therefore the likely presence of parasite antigen in these particular calcified lesions. However, parasite antigen has not been directly detected in these lesions, and whether the edema is associated with inflammation and the nature of the inflammation have not been established. It is not known whether the presence of calcium in a lesion is solely a visual marker of past or present pathology or plays a direct or indirect role in the induction of seizures. Direct calcium toxicity has been suggested and there are some data indicating that lesions that calcify are associated with increased seizure activity compared to those that fail to calcify. Calcium may also form an insoluble matrix that could release incorporated antigens at certain times. Direct injury to brain tissues associated with single calcified or non-calcified cysticercal granulomas is another possible reason for continued or recurrent seizure activity. This is suggested by the presence of gliosis around foci associated with seizure activity compared to clinically silent lesions as noted by the use of specific MRI magnetization transfer sequences. Another hypothesis is that edema can be caused by seizure activity itself. Focal edema has been documented in lesions in a few cases with partial status epilepticus from other causes. However, this finding is rare and the MRI pattern of edema associated with perilesional edema in cysticercosis is most consistent with vasogenic edema resulting from blood-brain barrier breakdown of the lesion. In contrast, the edema does not have the radio imaging appearance of cytotoxic edema resulting from cell swelling associated with prolonged seizures.

An ever-growing group of neurologists, parasitologists, and epileptologists believe human neurocysticercosis and parallel animal models offer a unique opportunity to understand basic mechanisms of seizures and the transition to chronic epilepsy and/or intractable epilepsy. Neuro-cysticercosis may well serve as a useful biomarker for epileptogenesis in humans. How early in the degenerative process different mechanisms are involved is central to understanding how epilepsy develops.

Certain infections result in or are exacerbated by calcification. For example, neurocysticercosis, is a specific form of the infectious parasitic disease cysticercosis which is caused by infection with *Taenia_solium,* a tapeworm found in pigs. Cysticercosis in the United States, which commonly presents in the form of neurocysticercosis, has been classified as a "neglected tropical disease", which commonly affects the poor and homeless and, in addition, also afflicts recent immigrants from countries affected by the disease. The tapeworm can be eradicated from the body but there may be residual effects. Neurocysticercosis occurs when hypercalcaemia cysts formed by the infection grow within the brain causing neurologic syndromes, such as epileptic seizures. Neurocysticercosis, most commonly, involves the cerebral cortex followed in prevalence by the cerebellum The cysts may rarely coalesce and form a tree-like pattern which is known as racemose. Neurocysticercosis, when involving the pituitary gland may result in multiple pituitary hormone deficiencies.

Tuberous Sclerosis Complex and Calcification

Certain neurological diseases, such as epilepsies, result from calcification. For example, tuberous sclerosis complex is a rare multisystem genetic disease caused by mutations of either of two genes, TSC1 and TSC2, which code for the tumor growth suppressor proteins, hamartin and turberin, respectively. The most serious intracranial manifestations are cortical tubers that calcify with aging producing autism spectrum disorder in a significant proportion of patients.

Tuberous sclerosis complex, also known as Bourneville's Disease is an autosomal dominant disorder that can be formed by spontaneous mutations in up to two-thirds of cases. The prevalence/clinical penetrance of tuberous sclerosis complex is now estimated to be from one in 6,000 to one in 12,000 live births. Overall, epilepsy and mental deficits are the most common neurological problems and tend to be more severe if manifested early. Three different mutations have been associated with the disorder, located on chromosomes 9, 11, and 16. Tuber Sclerosis Complex may also be caused by mutations of two genes known as TSC1 and TSC2. TSC1 and TSC2 are tumor suppressor genes whose function is to help regulate cell growth and differentiation. If they are altered by mutation, disturbed control of cell growth results in formation of tumors throughout the body. A characteristic radiological finding of tuberous sclerosis complex is the presence of benign congenital tumors in multiple organs. Cardiac rhabdomyoma, renal angiomyolipoma, and neurologic involvement encompassing cortical or subependymal tubers and white matter abnormalities are also common radiologic findings. The presence of pulmonary lymphangioleiomyomatosis, multifocal micronodular pneumocyte hyperplasia, or multiple renal cysts is also indicative of tuberous sclerosis complex.

Although recent advances in treatment have improved morbidity, the prognosis of tuberous sclerosis complex is still poor and nearly 40% of patients die by the age of 35 years. Much of the poor prognosis is related to neurological findings including: (1) cortical tubers; (2) subependymal nodules; (3) subependymal giant cell astrocytomas (SGCAs); and (4) white matter abnormalities.

Cortical tubers and/or subependymal nodules (SENs) are present in 95 to 100% of tuberous sclerosis complex patients. Commonly, these tubers and nodules become calcified. Calcification of SENs is frequent (93%) in patients with tuberous sclerosis complex, especially after 18 months of age, and an increase in size with time in 35% of patients. Calcification in tubers has been reported in 43 to 62% of patients and prevalence increases with age. However, unlike SENs, cortical tubers do not usually increase in size over time in adults, and remain proportional to the rest of the brain in growing children. Hypercalcification/calcinosis of cells, tissues, and intracellular and intracranial spaces caused by tuberous sclerosis complex, is highly associated with epileptogenesis and increased seizure activity. Generally, resection of calcified tubers is the standard of therapy for removal and reduction of epileptogenesis. At some point, seizures affect 80 percent of patients with tuberous sclerosis complex. These seizures are often intractable in nature.

It seems probable that the high occurrence of seizures and seizure-related disorders can be related to the high level of calcinosis in the tuberous sclerosis complex sufferer's brains. The present invention, fully described in the claims, shows that utilization of calcium chelators, such as bisphosphonates represents a viable, non-surgical treatment for reduction of intracellular and intracranial calcium, resulting in disease modification of seizures thus an improvement in cognitive development without the need for brain surgery.

Sturge-Weber Syndrome and Calcification

Sturge-Weber Syndrome (SWS) is another disease that is characterized by calcifications of the brain. Unlike, tuberous sclerosis complex, no clear evidence of heredity has been discovered in Sturge-Weber syndrome. Sturge-Weber syndrome is a rare neurological, eye, and skin disorder characterized by nervous system problems and a permanent birthmark, known as a Port Wine Birthmark (PWB), usually on the face. Sturge-Weber syndrome affects approximately 1 in 40,000 to 1 in 400,000 globally and fewer than 200,000 in the U.S. Sturge-Weber syndrome is caused by a somatic mutation of the GNAQ gene that occurs after conception and is not inherited. PWBs are caused by abnormally dilated capillaries in the skin, which produce red to purple discoloration. This feature is almost always present and usually involves the ophthalmic division (V1) of the trigeminal nerve. In its classical form the syndrome is characterized by: (1) congenital, usually unilateral, capillary naevus ('port-wine stain') affecting the face, particularly the supraorbital region, often associated with buphthalmos or glaucoma; (2) convulsions, usually contralateral to the side of the naevus; (3) typical intracranial calcifications adjacent to capillary malformations that become radiologically visible after infancy; (4) some degree of mental subnormality in the majority of the patients; and (5) Hemiparesis and homonymous hemianopia contralateral to the brain lesion in a substantial proportion of cases.

The radiological hallmark of the syndrome is double-contoured curvilinear calcification following a gyral pattern, becoming radiologically recognizable later in childhood and involving most frequently the occipital and parietal area. Histologic studies have shown that calcification in Sturge-Weber Syndrome appears to be related to a combination of gliosis due to chronic anoxia and venous hypertension along with altered vascular permeability of the abnormal vessels overlying the involved cortex. Wu, et al., demonstrated a link between severely diminished white matter perfusion, the presence of marked cortical calcification, and a higher seizure burden in children with Sturge-Weber Syndrome. These findings lend further support to prevailing theories regarding the development of calcification in Sturge-Weber Syndrome. These calcifications grow over time and are associated with further neurological deterioration.

Certain vascular conditions result in or are exacerbated by calcification, for example, Sturge-Weber Syndrome. Occurring in 1 in 50,000 newborns, Sturge-Weber Syndrome, sometimes referred to as encephalotrigeminal angiomatosis, is a rare congenital neurological and skin disorder indicated at birth by a facial angioma in Types I and II but more critically in Types I and III by leptomeningeal angiomas. It is caused by a somatically activating mutation in the GNAQ gene so occurs sporadically. The malformation of the blood vessels in the pia mater overlying the brain on the same side of the head as the birthmark resulting in calcification of tissue and loss of nerve cells in the cerebral cortex that leads to seizures and muscle weakness. The Calcinosis in the brain is the most serious consequence, which, for some, results in developmental and cognitive delays in over 50% of cases. At present, only symptomatic treatment is available, such as laser removal of birthmarks, anticonvulsant medications to control seizures, and monitoring of glaucoma with possible surgical intervention or prostaglandins to reduce intraocular pressure. The partial epilepsy may be controlled by drugs such as carbamazepine or valproate; however, in severe cases, neurosurgical removal of the epileptic focus in the brain may be necessary. The prognosis is dire, particularly for those with convulsive seizures resistant to drug treatment resulting in greater likelihood of cognitive impairment.

Much like Tuberous Sclerosis Complex, one of the hallmarks of Sturge-Weber Syndrome is the presence of intracranial/intracerebral calcinosis. This calcinosis often is associated with intractable seizures, seizure-related disorders, and difficult to control, chronic and debilitating headaches. The present invention, fully described in the claims, demonstrates that treatment of intracerebral calcinosis using Kamini™ is a viable treatment for Sturge-Weber Syndrome and other disorders characterized by calcinosis of the brain.

Loeb et al., has on more than one occasion demonstrated improvement of calcium-dependent epilepsy by using calcium chelating medications such as immediate-release bisphosphonates. The present invention, fully described in the claims, uses this principle to incorporate Kamini™ for the treatment of headaches and seizures related to Neurocysticercosis, Tuberous Sclerosis Complex, and Sturge-Weber Syndrome.

There is an unmet need to address the calcinosis associated with these diseases. One approach would be to use binders of free calcium to keep the calcium bound in stable hydroxyapatite form sealing the harmful deposits. Bisphosphonates like Kamini™ (disodium etidronate) are potent binders of free calcium in the body. Through calcium chelation, disodium etidronate can minimize the adverse effects of an over-supply of calcium in the body. However, chronic use of disodium etidronate and other bisphosphonates can break down the protective phospholipids layers in the esophagus and stomach and lead to ulceration, erosion, and perforation. The formulation of an enterically-coated disodium etidronate would allow the medicine to pass unaltered through the esophagus, stomach, and duodenum, then dissolve, and be absorbed in the proximal jejunum.

The present invention, fully described in the claims, provides a novel approach to the treatment of Neurocysticercosis, Tuberous Sclerosis Complex and Sturge-Weber Syndrome, based on success by one of the current inventors (Loeb) with the diagnosis and treatment of Fahr's disease. Fahr's Disease, known as Striopallidodentate Calcification, represents a trusted model when using intracranial/intracerebral calcinosis as a diagnostic and potential treatment avenue for calcium-related disorders.

Fahr's Disease is a rare disorder characterized by bilateral symmetrical calcification in the basal ganglia with or without involvement of the cerebellar dentate nucleus. Even though molecular genetics of Fahr's disease have not been studied extensively; the consensus view is that Fahr's Disease is most commonly transmitted as an autosomal dominant trait; but may also be passed on as an autosomal recessive trait or may occur sporadically. A Locus at 14q (IBGC1) has been suggested to be involved commonly. A second locus has been identified on chromosome 8 and a third on chromosome 2. A loss of function mutation in the gene encoding type III sodium-dependent phosphate transporter 2 (SLC20A2) located on chromosome 8 has also been reported as the molecular level to form the genetic basis for the pathophysiology of this disease. Fahr's can manifest in many different ways, but can be ordered into three basic categories: (a) Neurological with symptoms of (i) seizures, (ii) seizure disorders, (iii) dementia; (b) Movement with symptoms of (i) clumsiness, (ii) fatigability, (iii) unsteady gait; (c) Neuropsychiatric features such as (i) psychosis, (ii) depression, (iii) deterioration of intelligence.

One of the present inventors (Loeb) found that for Fahr's Disease there is a remarkable propensity for the accumulation of calcium and other multivalent cations in the basal ganglia and the dentate nucleus of man. Loeb also referred to these accumulations as "Brain Stones" and found they are composed mostly of hydroxyapatite, the same calcium-phosphate structure in normal bone. Moreover, there is direct association between brain calcification and progressive neurological symptoms. Conversely in patients treated with the bisphosphonate, disodium etidronate, there is symptomatic improvement of seizures, headaches, and Parkinsonian symptoms. Therefore, the diagnosis and treatment of Fahr's disease is the basis of a trusted model for the present invention, fully described in the claims.

The selection of disodium etidronate rather than a second-generation bisphosphonate such as alendronate is confirmed by a follow-on study that achieved symptomatic relief in a large patient population but not as significantly as with disodium etidronate. Much like Fahr's Disease, Tuberous Sclerosis Complex, and Sturge-Weber Syndrome, one of the hallmarks of Neurocysticercosis is the presence of intracranial/intracerebral calcification. This calcinosis often leads to intractable seizures, seizure-related disorders, and headaches. The present invention, fully described in the claims, demonstrates that treatment of intracerebral calcinosis using Kamini™ is a viable treatment for Neurocysticercosis and other disorders characterized by calcinosis of the brain.

BRIEF DESCRIPTION OF THE FIGURES

It is to be understood that both the foregoing general description and the following detailed description are exemplary and explanatory only and not restrictive of the invention, as claimed.

A full and enabling disclosure of the present invention, fully described in the claims, including the best mode thereof, directed to one of ordinary skill in the art, is set forth in the specification, which makes reference to the appended figures, which are not necessarily drawn to scale, and wherein:

Figure 1:
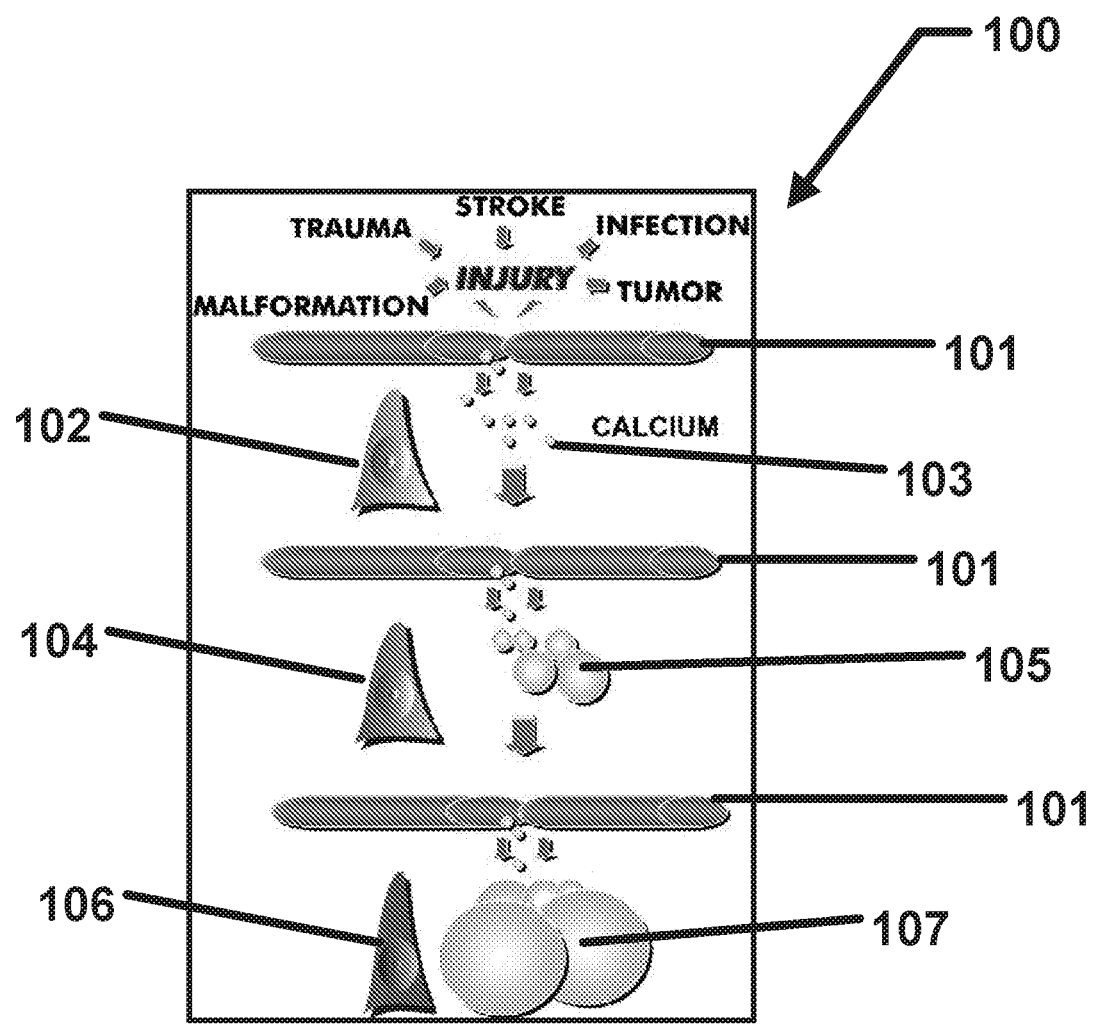
FIG. 1. Schematic Diagram of General Process of Disease Causing Calcinosis.

The system described here enables a person (sometimes called a physician) to diagnose and treat interactively a patient with a calcinosis condition, such as Neurocysticercosis, Tuberous Sclerosis Complex, or Sturge-Weber Syndrome. For instance, the system described, here can be used to instruct healthcare personnel in a method, to modify disease progression, resolve symptoms, reduce seizures, alleviate pain, and maintain positive attitude.

DETAILED DESCRIPTION OF THE PREFERRED EMBODIMENT

Reference now will be made in detail to embodiments of the invention, one or more examples of which are illustrated more fully in the drawings. Each example is provided by way of explanation of the invention, not limitation of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art. In fact, it will be apparent to those skilled in the art that various modifications and variations can be made in the present invention, fully described in the claims, without departing from the scope or spirit of the invention. For instance, features illustrated or described as part of one embodiment can be used with another embodiment and such variations come within the scope of the appended claims and their equivalents.

Like numbers refer to like elements to those skilled in the art. Like numbers refer to like elements throughout. The term "exemplary" as used throughout this document is defined to mean "example." It will be appreciated that terms such as "left", "right", "top", "bottom", "inwardly", "outwardly", "front", "inner", "up", and "down" and other positional descriptive terms used herein below are used merely for ease of description and refer to the orientation of the components as shown in the Figures. It should be understood that any orientation of the elements described herein is within the scope of the present invention, fully described in the claims.

As desired, embodiments of the invention may include the real-time, interactive medical system with more or less of the components illustrated.

The invention is described below with reference to block and flow diagrams of systems, methods, apparatuses, and/or computer program products according to exemplary embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general-purpose computer, a special-purpose computer, a mobile device, such as a laptop or smartphone, a processor, or other programmable data processing apparatus to produce a particular machine, such that the instructions that execute on the computer, processor, or other programmable data processing apparatus, create means for implementing one or more functions specified in the flow diagram block or blocks, These computer program instructions may also be stored in a non-transitory computer-readable memory that can direct a computer or other programmable data processing apparatus to function in a particular manner, such that the instructions stored in the non-transitory computer-readable memory produce an article of manufacture including instruction means that implement one or more functions specified in the flow diagram block or blocks. As an example, embodiments of the invention may provide for a computer program product, comprising a non-transitory computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. Alternately the computer operating system, all data storage, and computer instructions for executing the interactive operations may be embodied on a single machine in a hyperconvergent arrangement. In one embodiment, a handheld device, such as a smartphone, could be used to deliver said computer program instructions so that persons could pose questions regarding clinical care and procedures via said handheld device. These computer-implemented processes could be virtualized in a cloud-based environment.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

While the invention has been described in connection with what is presently considered to be the most practical embodiment and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

The term "calcinosis" as used herein refers to the deposition of calcium in soft tissue, for example, the brain. Such abnormal deposition results from the buildup of calcium salts in the tissue, referred to as calcification, following the abnormal buildup of calcium ions in the blood, hypercalcemia. Normally calcium is deposited in bone or teeth but deposition in soft tissue is often the pathophysiology for numerous diseases.

The term "blockchain technology" as used herein means use of a distributed network ledger using public key cryptography to cryptographically sign transactions that are stored on a distributed ledger with the ledger consisting of cryptographically linked blocks of transactions. Such directly verifiable transactions facilitate drug manufacture logistics, in conformance with 21 CFR211 C (g), and clinical drug delivery.

The term "bolus" as used herein means that release of a significant amount of the bisphosphonates is achieved at the site of initiation/release.

The terms "continuous" or "continuously," as used herein, mean at regular specified intervals. For example, a continuous schedule according to a dosing regimen of once weekly means that the active is given one time per week for an unspecified period of time or for as long as treatment is necessary.

The term "nutrient," as used herein, means any nutritional or dietary supplement including but not limited to vitamins, minerals, amino acids, herbs or other botanicals, or concentrates, metabolites, constituents, extracts, or combinations of the same.

The term "pharmaceutical composition," as used herein, means an oral dosage form comprised of a safe and effective amount of a bisphosphonate active ingredient and one or more pharmaceutically-acceptable excipients, including at least one agent serving as an enteric coating. The pharmaceutical compositions described herein are comprised of from 0.5% to 75%, preferably from 1% to 40% of a bisphosphonate active ingredient and from 25% to 99.5%, preferably from 60% to 99% of pharmaceutically-acceptable excipients including at least one enteric-coating agent.

The term "safe and effective amount," as used herein, means an amount of a compound or composition high enough to significantly positively modify the symptoms and/or condition to be treated, but low enough to avoid serious side effects (at a reasonable risk/benefit ratio), within the scope of sound medical judgment. The safe and effective amount of active ingredient for use in the method of the invention herein will vary with the particular condition being treated, the age and physical condition of the patient to be treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "sustained release" means that the bisphosphonate is not substantially released at the site of initiation but continues to be released from the initiation site throughout the remainder of the GI tract with preferred dissolution and absorption in the proximal jejunum.

The term "pharmaceutically effective absorption" as used herein means an amount of an enteric-coating compound high enough to significantly bind the metal ions and minerals in food but low enough not to significantly alter absorption of the bisphosphonate as compared to absorption in the fasted state. That is, absorption is similar with or without food. Given the high variability of bisphosphonate absorption, fed exposure within about 50% of fasting exposure is expected to be pharmaceutically effective absorption.

The term "oral dosage form," as used herein, means any pharmaceutical composition intended to be administered to the lower gastrointestinal tract of a human or other mammal via the mouth of said human or other mammal. For the purposes of the present invention, fully described in the claims, the delivered form can be in the form of a compressed tablet containing granules or particles of a bisphosphonate, a capsule (e.g., soft gelatin or hard gelatin, consisting of starch, or hydroxypropylmethylcellulose which contains beads, particles, or suspensions of the bisphosphonate, or a dry mix containing granules or particles of bisphosphonate for making a reconstituted suspension in water (e.g., a sachet).

The term "unit dose" or "unit dosage" means a dosage form containing an amount of pharmaceutical active or nutrient suitable for administration in one single dose, according to sound medical practice. The present invention, fully described in the claims, is particularly useful for the administration of unit doses in the form of tablets and capsules.

The term "gastrointestinal tract" or "GI tract," as used herein, relates to the alimentary canal, i.e., the musculo-membranous tube about thirty feet in length, extending from the mouth to the anus. The term "upper gastrointestinal tract," as used herein, means the buccal cavity, the pharynx, the esophagus, and the stomach. The term "lower gastrointestinal tract," as used herein, means the small intestine and the large intestine.

The term "small intestine," as used herein, means the part of the lower gastrointestinal tract consisting of the duodenum, the jejunum, and the ileum, i.e., that portion of the intestinal tract just distal to the duodenal sphincter of the fundus of the stomach and proximal to the large intestine.

The term "large intestine," as used herein, means the part of the lower gastrointestinal tract just distal to the small intestine, beginning with the cecum, including the ascending colon, the transverse colon, the descending colon, the sigmoid colon, and the rectum.

The terms "bisphosphonate" and "diphosphonate," as used herein, include acids, salts, esters, hydrates, polymorphs, hemihydrates, solvates, and derivatives thereof. The bisphosphonates of the present invention, fully described in the claims, include those preferred compounds containing a nitrogen atom. Non-limiting examples of bisphosphonates useful herein include the following: 1-hydroxyethane, 1,1-diphosphonic acid (Etidronate) as described in U.S. Pat. No. 6,4324,413, to Jeffrey A. Loeb, issued Aug. 13, 2002, which is incorporated by reference in its entirety. Also included in the definition of bisphosphonates is disodium etidronate which is a non-nitrogen containing bisphosphonate.

In one embodiment of the invention, the bisphosphonate is selected from the group consisting of etidronate, and salts, esters, hydrates, hemihydrates, polymorphs, and solvates thereof, and combinations thereof.

It should be noted that the terms "bisphosphonate" and "bisphosphonates," as used herein in referring to the therapeutic agents of the present invention, fully described in the claims, are meant to also encompass diphosphonates, bisphosphonic acids, and diphosphonic acids, as well as salts, esters, hydrates, polymorphs, hemihydrates, solvates, and derivatives of these materials.

Non-limiting examples of bisphosphonate salts useful herein include those selected from the group consisting of alkali metal, alkaline metal, ammonium, and mono-, di-, tri-, or tetra-$C1$-$C_{30}$-alkyl-substituted ammonium. Preferred salts are those selected from the group consisting of sodium, potassium, and ammonium salts.

The amount of bisphosphonate active ingredient contained in the oral dosage forms of the present invention, fully described in the claims, will depend on the particular bisphosphonate selected and the continuous dosing schedule upon which the bisphosphonate is dosed to the patient. Continuous dosing schedules of daily, weekly, twice monthly, three times per month, and once monthly are non-limiting examples of dosing regimens suitable for use with the oral dosage forms of the present invention, fully described in the claims. The terms "three times per month" or "thrice monthly" mean that an oral dosage form is administered thrice, i.e., three times, during a monthly calendar period. In a thrice monthly schedule, the oral dosage forms may be administered on three consecutive days, or once about every nine to eleven days. The terms "twice per month" or "twice monthly" mean that an oral dosage form is administered twice, i.e., two times, during a monthly calendar period. In a twice monthly regimen, the oral dosage forms may be administered on consecutive days or once about every fourteen to sixteen days. The terms "monthly" or "once monthly" mean that an oral dosage form is administered once, i.e., one time during a monthly calendar period, that is, about every 28 to 31 days.

The use of a specific nomenclature in referring to the bisphosphonate or bisphosphonates is not meant to limit the scope of the present invention, fully described in the claims, unless specifically indicated. Mixed nomenclature is currently in use by those of ordinary skill in the art, for example reference to a specific weight or percentage of a bisphosphonate active ingredient is on an anhydrous monosodium salt basis for etidronate. For the present invention, fully described in the claims, the phrase "about 35 mg of a bone etidronate inhibiting bisphosphonate selected from the group consisting of etidronate, pharmaceutically acceptable salts thereof, and mixtures thereof, on an anhydrous monosodium salt basis" means that the amount of the bisphosphonate compound selected is calculated based on about 35 mg of anhydrous etidronate monosodium salt. Generally, the oral dosage forms of the present invention, fully described in the claims, will contain from about 1 mg to about 500 mg of a bisphosphonate on an anhydrous weight basis. When the bisphosphonate is dosed on a daily basis, the oral dosage form contains from about 5-15 mg/kg/day bisphosphonate on an anhydrous weight basis. When the bisphosphonate is dosed on a weekly basis, the oral dosage form contains from about 10 mg to about 200 mg bisphosphonate on an anhydrous weight basis. When the bisphosphonate is dosed on a twice monthly basis, the oral dosage form contains from about 20 mg to about 300 mg bisphosphonate on an anhydrous weight basis. When the bisphosphonate is dosed three times per month, the oral dosage form contains from about 15 mg to about 250 mg bisphosphonate on an anhydrous weight basis. When the bisphosphonate is dosed on a monthly basis, the oral dosage form contains from about 50 mg to about 500 mg on an anhydrous weight basis.

When the bisphosphonate active ingredient is disodium etidronate, a daily oral dosage form of the present invention, present invention, fully described in the claims, contains from about 5-15 mg/kg/day etidronate on an etidronate anhydrous monosodium salt basis. A weekly oral dosage form contains from about 10 to about 50 mg etidronate on an etidronate anhydrous monosodium salt basis. A twice monthly oral dosage form contains from about 20 to about 100 mg etidronate, preferably about 75 mg on an etidronate anhydrous monosodium salt basis. An oral dosage form that is administered three times per month contains from about 15 to about 75 mg etidronate, preferably about 50 mg etidronate on an etidronate anhydrous monosodium salt basis. A monthly oral dosage form contains from about 50 to about 200 mg etidronate, preferably from about 100 to about 175 mg etidronate, and more preferably about 150 mg etidronate on an etidronate anhydrous monosodium salt basis.

The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms.

The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is formed, each successive donor atom that binds creates a ring containing the metal atom. A chelating agent may be bidentate, tridentate, tetradentate, etc., depending upon whether it contains two, three, four, or more donor atoms capable of binding to the metal atom.

In homogeneous dilute solutions, the equilibrium constant for the formation of the complex from the solvated metal ion (e.g., calcium) and the chelating agent in its fully dissociated form is called the formation or stability constant, K. The practical significance of formation constants is that a high log K value means a large ratio of chelated to unchelated (or free) metal ion, when equivalent amounts of metal ion and chelating agent are present. Higher ratios (or difference if K is expressed in log units) of the chelating agent and the bisphosphonate complexation constants are preferred in order to have nearly all of the metal ion complexed to the chelating agent instead of the bisphosphonate. For example, for equal molar amounts of both bisphosphonate and the enteric-coating chelating agent, in order for the metal ions to be 99% complexed to the chelating agent, the chelating agent must have a log K which is at least 4 units higher than the bisphosphonate-metal ion complex. The other technique which can be used to favor the chelating agent-metal ion complex over that of the bisphosphonate-metal ion complex is to add a molar excess of the chelating agent which relies on the law of mass action to favor formation of the chelating agent-metal ion complex.

Although pH and solution concentration can affect the formation constant, in general, the log K of the enteric-coating chelating agent is preferably at least equal to that of the bisphosphonate. In other instances, the log K of the chelating agent is 2 to 5 units higher than that of the bisphosphonate. In other instances, the chelating agent is present at a molar excess to that of the bisphosphonate. The chelating agent in such instances is present in at least a 2:1 molar ratio of the chelating agent to bisphosphonate.

The enteric-coating chelating agent may be soluble or insoluble in the gastrointestinal tract as long as it is readily available for complexation with metal ions in the food. In one instance, a chelating agent that is soluble in the gastrointestinal tract is used because chelating agents that are poorly soluble may be too slowly available to complex a significant portion of the calcium in the co-administered food. In other instances, the chelating agent should have solubility comparable to or greater than that of the bisphosphonate so that it can be present in its complexing form at concentrations at least equal to that of the bisphosphonate. The use of an enterically-coated bisphosphonate, i.e., Kamini, eliminates the issue with taking bisphosphonates with milk which would be an issue with children that are consuming milk-containing products.

Various classes of enteric-coating chelating agents are suitable for use in the present invention, fully described in the claims. Non-limiting examples of these classes include polyphosphates (e.g., sodium tripolyphosphate, hexametaphosphoric acid, sodium acid pyrophosphate, sodium pyrophosphate, tetra sodium pyrophosphate, sodium hexametaphosphate, sodium metaphosphate); aminocarboxylic acids (e.g., ethylenediaminetetraacetic acid (EDTA), 1,2-bis(2-amino-phenoxy)ethane-N,N,N'N'-tetraacetic acid (EGTA), ethylenebis (oxyethylenenitrilo)tetraacetic acid (BAPTA), N-(hydroxyethyl)-ethylenediaminetriacetic acid (HEDTA), diethylenetriaminepentaacetic acid (DTPA), N-dihydroxyethylglycine (2-HxG), ethylenebis(hydroxyphenyl-glycine) (EHPG), glutamic acid, aspartic acid, glycine, lysine); 1,3-diketones (e.g., acetylacetone, trifluoroacetylacetone, thenoyltrifluoroacetone, ascorbic acid); hydroxycarboxylic acids (e.g., tartaric acid, citric acid, malic acid, gluconic acid, ferulic acid, lactic acid, glucuronic acid); polyamines (e.g., dietheylenetriamine, triethylenetriamine); aminoalcohols (e.g., triethanolamine, N-hydroxyethylethylene-diamine, aminoethylethanolamine (AEEA); phenols (e.g., disulfopyrocatechol, chromotropic acid); aminophenols (e.g., oxinesulfonic acid); Schiff bases (e.g., disalicylaldehyde 1,2-propylenediimine); tetrapyrroles (e.g., tetraphenylporphin, phthalocyanine); silicates (aluminum calcium silicate, calcium silicate, sodium aluminosilicate sodium calcium aluminosilicate (hydrates), tricalcium silicate); sulfur compounds (e.g., potassium ethyl xanate, sodium diethyldithiocarbamate, diethyl dithiophosphoric acid, thiourea, magnesium sulfate); synthetic macrocyclic compounds (e.g., hexamethyl-[14]-4,11-dieneN$_4$, 2.2.2-cryptate); polymers (e.g., polyethyleneimines, polymethacryloylacetone, poly (p-vinylbenzyliminodiacetic acid)), phosphonic acids (e.g., nitrilotrimethylenephosphonic acid, ethylenediaminetetra- (methylenephosphonic acid), hydroxyethylidenediphosphonic acid).

In one embodiment, the enteric-coating chelating agent is selected from the group consisting of EDTA, citric acid, malic acid, tartaric acid, lactic acid, adipic acid, succinic acid, aspartic acid, glutamic acid, lysine, sodium hexametaphosphate, and combinations thereof. In another embodiment, the chelating agent is EDTA, citric acid, or sodium hexametaphosphate.

In another embodiment of the invention, a monodentate enteric-coating chelating agent which often precipitate as metal ion complexes, may be used in place of a polydentate chelating agent. Suitable monodentate complexing agents include, but are not limited to, phosphates (e.g., sodium phosphate, sodium aluminum phosphate, sodium acid phosphate, dipotassium phosphate, disodium phosphate, monobasic) and carboxylic acids (e.g., acetic acid).

The amount of enteric-coating chelating agent present in the oral dosage form of the present invention, fully described, in the claims, will depend, on the particular chelating agent or agents (i.e. mixtures of chelating agents) selected, the amount of bisphosphonate active ingredient present in the oral dosage form, and the specific portion of the lower GI tract where delivery of the chelating agent and/or bisphosphonate active ingredient is desired. After the ingestion of milk, it has been shown in the art that the concentration of calcium decreases over the length of the lower GI tract, beginning with the small intestine and, proceeding through to the end of the large intestine. Thus, for example, a lower concentration of a particular enteric-coating chelating agent may be required to effect delivery of the bisphosphonate to the transverse colon, as compared with the concentration of that same chelating agent required to effect delivery of the bisphosphonate to the terminal ileum, given the same dose of bisphosphonate active ingredient.

Generally, the oral dosage forms of the present invention, fully described in the claims, will contain a safe and effective amount of an enteric-coating chelating agent suitable for achieving the desired protective chelating effect, that is, chelating the residual metal ions that are present in the gastrointestinal tract from food at the site of delivery without significantly affecting the absorption of the bisphosphonate had no food been present. In one embodiment, the oral dosage form contains from about 10 mg to about 1000 mg of a chelating agent per unit dose. In another embodiment, the oral dosage forms contain from about 10 mg to about 500 mg of a chelating agent per unit dose. When the chelating agent is disodium EDTA, the preferred range is from about 55 mg to about 500 mg, preferably from about 75 mg to about 250 mg per unit dose. When the chelating agent is citric acid, the preferred range is from about 100 mg to about 1000 mg, preferably from about 250 mg to about 500 mg per unit dose.

A human or other mammal suffering from diseases or disorders involving calcium and phosphate metabolism can be successfully treated by the delivery of the bisphosphonate active ingredient to the lower GI tract of said human or other mammals. The novel dosage forms described herein effect delivery to the lower GI tract, and prohibit the undesired release of bisphosphonate in the mouth, pharynx, esophagus, and/or stomach, thereby prohibiting the erosion, ulceration, or other like irritation of the epithelial or mucosal layers of these tissues. In some instances, it may be desirable to effect delivery of the bisphosphonate and the chelating agent to the small intestine or a particular segment of the small intestine, (e.g., the terminal ileum). In other cases, it may be desirable to effect delivery of the bisphosphonate and the chelating agent to the entire lower GI tract or to a segment of the GI tract, beginning with delivery to the small intestine and continuing with delivery if needed to the large intestine. In yet other cases it may be desirable to effect a bolus delivery of the bisphosphonate and chelating agent to the lower GI or to specific segments of the lower GI tract. In one embodiment of the invention, delivery of the active beginning in the small intestine and continuing through to the large intestine may be accomplished through the use of sustained release formulations known to those skilled in the art. Such sustained release formulations are designed to slow the release of the bisphosphonate and the chelating agent over a specified time period, as the oral dose form progresses through the lower GI tract. In still other instances, it may be desirable to achieve delivery of the bisphosphonate and the chelating agent to the large intestine or a particular segment thereof (e.g., the ascending colon). In still other instances, it may be desirable to deliver the enteric-coating chelating agent and the bisphosphonate in a bolus amount to the large intestine. In still other instances, it may be desirable to deliver the chelating agent to one segment of the lower GI tract, and to deliver the bisphosphonate to a different segment of the lower GI tract. For example, it may be desirable to deliver the chelating agent to the terminal ileum and the bisphosphonate to the ascending colon.

The term "delayed release," as used herein, refers to a delivery of a bisphosphonate active ingredient and an enteric-coating chelating agent which is achieved by formulating the pharmaceutical composition comprising the bisphosphonate and the enteric-coating chelating agent so that their release will be accomplished at some generally predictable location in the lower GI tract more distal to that which would have been accomplished had there been no alteration in the delivery of the bisphosphonate.

In another embodiment of the invention, the bisphosphonate and the enteric-coating chelating agent may be administered to a mammal subject by way of more than one oral dosage form, each of which comprises a means for delivering the contents of said oral dosage form to the lower GI tract. For example, a patient may take a unit dosage of a bisphosphonate, followed by a separate unit dose containing the enteric-coating chelating agent.

In yet another embodiment the enteric-coating chelant and bisphosphonate are released rapidly and as close to simultaneously as possible. This causes the local concentration of enteric-coating chelating agent to be higher in relationship to the metal ions in the food. The higher local concentration of chelating agent in the environment where the active is released may more effectively complex the metals in the food and facilitate absorption of the bisphosphonate. This can be conveniently achieved from a single tablet Various means for targeting release of the bisphosphonate and the enteric-coating chelating agent in the lower GI tract are suitable for use in the present invention, fully described in the claims. Non-limiting examples of means for delivery to the lower GI tract include pH triggered delivery systems, dose forms from which the release of drug is triggered by the action of bacterial enzymes, and time dependent delivery systems.

In some cases, it may be desirable to initiate release of the bisphosphonate and enteric-coating chelating agent primary in the proximal jejunum. In other instances, it is desirable to primarily initiate release of the bisphosphonate and enteric-coating chelating agent in the mid-jejunum and/or the terminal ileum. In yet other cases, it may be desirable to provide a sustained release of the bisphosphonate and the enteric-coating chelating agent primarily in the jejunum throughout the terminal ileum. For primary colonic delivery, it may be desirable to initiate release of the bisphosphonate and enteric-coating chelating agent in the ascending and/or transverse colon.

One embodiment of the present invention, fully described in the claims, involves coating (or otherwise encapsulating) the bisphosphonate and the enteric-coating chelating agent (s) with a substance which is not broken down, by the gastrointestinal fluids to release the bisphosphonate until a specific desired point in the intestinal tract is reached.

In one embodiment, delayed release of the pharmaceutical composition is achieved by coating the tablet, capsule, or particles, granules, or beads of the bisphosphonate and the enteric-coating chelating agent with a substance which is pH dependent, i.e., broken down or dissolves at a pH which is generally present in the lower GI tract, but not present in the upper GI tract (i.e., the mouth, buccal cavity, pharynx, esophagus, or stomach).

In some cases, it may be desirable that the bisphosphonate and the enteric-coating chelating agent are released at a particular location in the small or large intestine. In other cases, it may be desirable to release the bisphosphonate and the enteric-coating chelating agent independently at different locations within the lower GI tract. For example, it may be desirable to release the enteric-coating chelating agent in the ascending colon, and the bisphosphonate in the transverse colon. When targeted release of the bisphosphonate and the enteric-coating chelating agent together or separately in particular locations within the lower GI tract is desired, the selection of the coating material and/or the method of coating or otherwise combining the bisphosphonate and the enteric-coating chelating agent with the selected coating material or other pharmaceutically-acceptable excipients may be varied or altered as is described herein, or by any method known to one skilled in the art.

The ultimate site of and/or the rate of delivery in the lower GI tract can be satisfactorily controlled by one skilled in the art, by manipulating any one or more of the following: (a) the active ingredient proper; (b) the type and level of disintegrant; (c) the type of coating, the type and level of excipients added to the coating and the concomitant desirable thickness and permeability (swelling properties) of the coating; (d) the time dependent conditions of the coating itself and/or within the coated tablet, particle, bead, or granule; (e) the particle size of the granulated active ingredient; and (f) the pH dependent conditions of the coating itself and/or within the coated tablet, particle, bead, or granule.

In particular, solubility, acidity, and susceptibility to hydrolysis of the different bisphosphonate active ingredients. In particular, solubility, acidity, and susceptibility to hydrolysis of the different bisphosphonate active ingredients, such as acid addition salts, salts formed with the phosphonic group (e.g., alkali metal salts, alkaline earth metal salts, etc.), and esters (e.g., alkyl, alkenyl, aryl, arylalkyl) may be used as guidelines for the proper choice. In addition, suitable pH conditions might be established within the coated tablets, particles, granules, or beads by adding a suitable buffer to the active ingredient in accordance with the desired release the active ingredient in accordance with the desired release pattern.

Besides the above-mentioned variations in order to obtain the desired release pattern, the excipients may also be varied, as long as they do not affect the activity of the particular bisphosphonate selected.

One embodiment of the present invention, fully described in the claims, is delivered to the lower GI tract utilizing a pH dependent enteric coating material made from a partly methyl esterified methacrylic acid polymer. The oral dosage form can be in the form of an enteric coated compressed tablet made of granules or particles of active ingredient or a gelatin capsule which contains beads or small particles of active ingredient which have themselves been enterically coated.

Any enteric coating which is insoluble at a pH below 5.5 (i.e., that generally found in the mouth, pharynx, esophagus, and stomach), but soluble at pH 5.5 or higher (i.e., that present in the small intestine and the large intestine) can be used in the practice of the present invention, fully described in the claims. Accordingly, when it is desired to effect delivery of the bisphosphonate and the chelating agent to the small intestine, any enteric coating is suitable which is wholly- or partially-insoluble at a pH below 5.5 and soluble at a pH 5.5 or above.

The enteric coating must be applied to the compressed tablet, the capsule (e.g., gelatin, starch, or hydroxypropylmethylcellulose) and/or the beads, particles or granules of active ingredient in a sufficient thickness so that the entire coating does not dissolve in gastrointestinal fluids at a pH below 5.5, but does dissolve at a pH of 5.5 or above. The dissolution or disintegration of the excipient coating generally does not occur until the entry of the coated dosage form into the small intestine.

It is expected that any anionic polymer exhibiting the requisite pH-dependent solubility profile can be used as an enteric coating in the practice of the present invention, fully described in the claims, to achieve delivery of the bisphosphonate and chelating agent to the lower GI tract. The coating chosen must be compatible with the particular bisphosphonate active ingredient selected. The preferred polymers for use in the present invention, fully described in the claims, are anionic carboxylic polymers. It is particularly preferred that the polymers are acrylic polymers, more preferably partly methyl-esterified methacrylic acid polymers, in which the ratio of free anionic carboxyl groups to ester groups is about 1:1.

In another embodiment as the ultimate locus of action of the bisphosphonate drug is the locus of the calcinosis in the brain, the delivery is intranasal or directly into the cerebral spinal fluid such to the above consideration to protect the delivery pathway from irritation.

FIG. 1 shows in schematic form, 100, the general process of disease causing calcinosis. Intracranial calcifications can form from various injuries (infection ischemia, and trauma) and are often the result of rare and orphan, genetic disorders that affect the brain. Intracerebral calcifications develop over months to years following this injury, and range in size from large, macroscopic "brain stones" to microscopic perivascular accumulations. They come from precipitation of leaked calcium from injured blood vessels through a breakdown in blood-brain barrier, 101, and from large, macroscopic "brain stones", 107, to microscopic perivascular accumulations, 103. The calcinosis results from precipitation of leaked calcium from injured blood vessels through a breakdown in blood-brain barrier, 101, and enlarge over time as shown, 103, 105, and 107. Neurons are increasingly affected, 102, 104, and 106. Areas where calcinoses are most commonly concentrated are in the basal ganglia in diseases such as Fahr's Disease, the cerebral cortex, cerebellar nuclei, and within tumors. Molecular analysis shows they are composed predominantly of hydroxyapatite, the same calcium phosphate complex present in bone and teeth.

Figure 2:
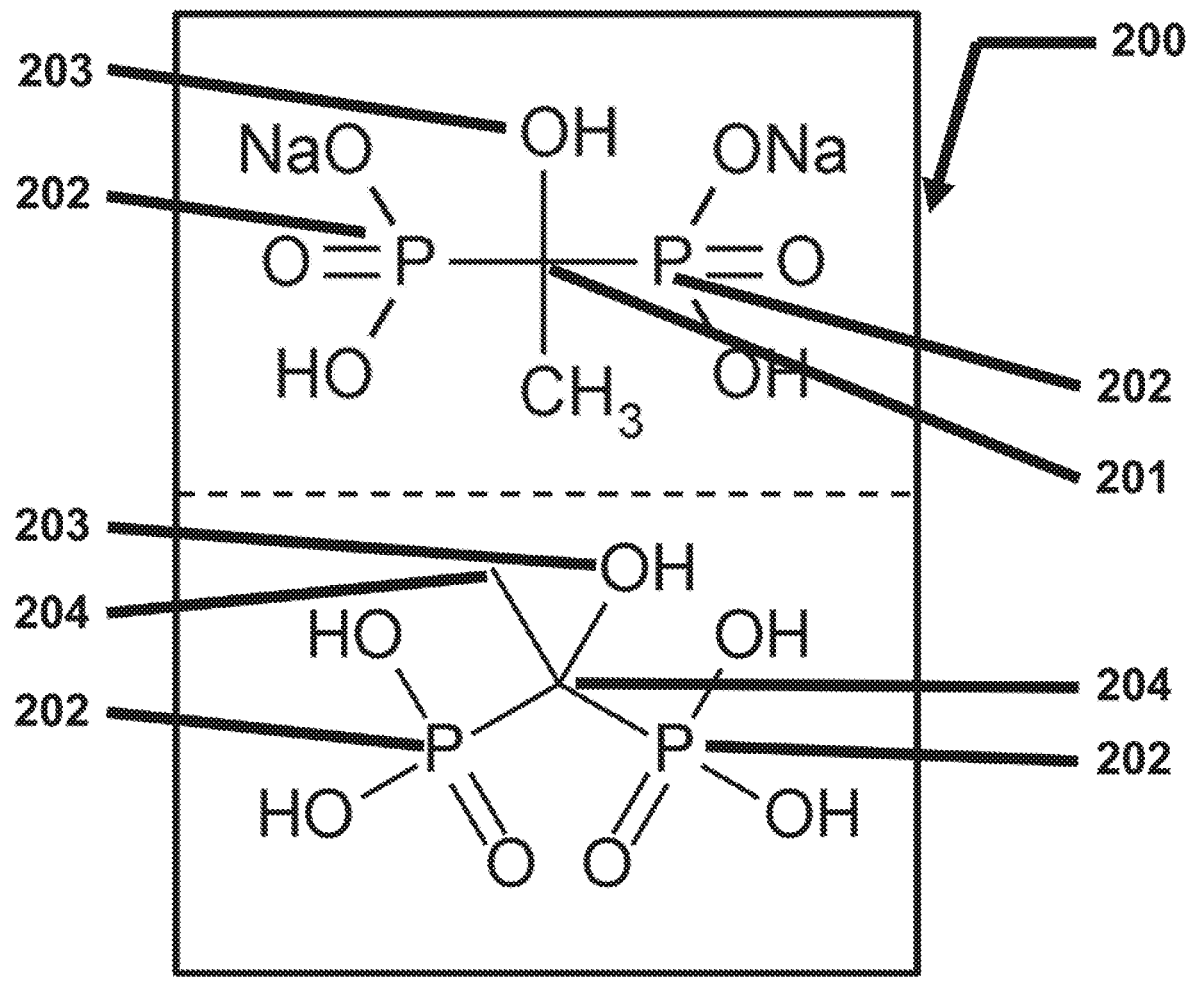
FIG. 2. Schematic Diagram of Structure of Kamini™ (disodium etidronate with enteric-coated extended release formulation).

FIG. 2 shows the structural arrangement of etidronic acid (1-hydroxyethane 1,1-diphosphonic acid abbreviated HEDP), which forms the basis for Na2HEDP in the novel pharmaceutical compound, Kamini™ (enterically-coated disodium etidronate). The chemical structure as detailed in FIG. 2 shows the basis for clinical activity. Disodium etidronate is a synthetic therapeutic diphosphonate analogue of endogenous pyrophosphate. As a member of the family of drugs known as bisphosphonates, disodium etidronate differs from endogenous pyrophosphate in its resistance to enzymatic hydrolysis. Disodium etidronate adsorbs to hydroxyapatite cells and reduces the number of osteoclasts, thereby inhibiting abnormal bone resorption. Disodium etidronate acts primarily on bone. It can inhibit the formation, growth, and dissolution of hydroxyapatite crystals and their amorphous precursors by chemisorption to calcium phosphate surfaces. Inhibition of crystal resorption occurs at lower doses than are required to inhibit crystal growth. Both effects increase as the dose increases. Disodium etidronate is not metabolized. The amount of drug absorbed after an oral dose is approximately 3%. In normal subjects, plasma half-life ($t_{1/2}$) of etidronate, based on non-compartmental pharmacokinetics is 1 to 6 hours. Within 24 hours, approximately half the absorbed dose is excreted in urine; the remainder is distributed to bone compartments from which it is slowly eliminated. Animal studies have yielded bone clearance estimates up to 165 days. In humans, the residence time on bone may vary due to such factors as specific metabolic condition and bone type. Unabsorbed drug is excreted intact in the feces. Preclinical studies indicate immediate-release etidronate disodium does not significantly cross the blood-brain barrier. The molecular weight of disodium etidronate is 249.99 g/mol. Most drugs are absorbed via the gastrointestinal tract by passive diffusion in their unionized state. The pH of the small intestine determines the degree of ionization and hence controls the efficiency of absorption; this is the basis of the pH-partition theory of drug absorption. For this reason, Kamini™ was formulated to have a pH that is ideal to allow for optimum absorption of active pharmaceutical ingredient in the proximal jejunum. The normal pH of the proximal jejunum ranges from 4.2 to 6.6.

FIG. 2 shows in schematic form, 200, two stereochemical versions of disodium etidronate. FIG. 2 shows how the chemical structure of disodium etidronate is its basis for clinical activity. Like their natural analogue PPi (pyrophosphate), bisphosphonates have a very high affinity for bone mineral because they bind to hydroxyapatite crystals. Bisphosphonates are preferentially incorporated into sites of active bone remodeling, as commonly occurs in conditions characterized by accelerated skeletal turnover. In addition to their ability to inhibit calcification, bisphosphonates inhibit hydroxyapatite breakdown, thereby effectively suppressing bone resorption. This fundamental property of bisphosphonates has led to their utility as clinical agents. More recently, it has been suggested that bisphosphonates also function to limit both osteoblast and osteocyte apoptosis.

The core structure of bisphosphonates differs only slightly from PPi in that bisphosphonates contain a central nonhydrolyzable carbon, 201; the phosphate groups, 202, flanking this central carbon are maintained. Nearly all bisphosphonates in current clinical use also have a hydroxyl group, 203, attached to the central carbon (termed the $R^1$ attached to the flanking phosphate groups, 202, provide bisphosphonates with a strong affinity for hydroxyapatite crystals in bone (and are also seen in PPi), whereas the hydroxyl motif, 203, further increases a bisphosphonate's affinity for hydroxyapatite. Collectively, the phosphate and hydroxyl groups create a tertiary rather than a binary interaction between the bisphosphonate and the bone matrix, giving bisphosphonates their remarkable specificity for bone. Although the phosphate and hydroxyl groups, 203, are essential for bisphosphonate affinity for bone matrix, the final structural moiety (in the $R^2$), 204, bound to the central carbon is the primary determinant of a bisphosphonate's potency for inhibition of bone resorption. The presence of a nitrogen or amino group increases the bisphosphonate's antiresorptive potency by 10 to 10,000 times relative to early non-nitrogen-containing bisphosphonates, such as etidronate. Recent studies delineate the molecular mechanism by which nitrogen-containing bisphosphonates inhibit osteoclast activity. In the present invention, more fully described in the claims, the novel compound, Kamini™, limits the effect on osteoclasts due to potential adverse side effects (reduced bone turnover, osteomalacia, etc.). A critical pharmacological feature of all bisphosphonates is their extremely high affinity for, and consequent deposition into, bone relative to other tissues. This high affinity for bone mineral allows bisphosphonates to achieve a high local concentration throughout the entire skeleton. Accordingly, bisphosphonates have become the primary therapy for skeletal disorders characterized by excessive or imbalanced skeletal remodeling, in which osteoclast and osteoblast activities are not tightly coupled, leading to excessive osteoclast-mediated bone resorption.

Early non-affinity for bone mineral allows bisphosphonates to achieve a high local concentration throughout the entire skeleton. Accordingly, bisphosphonates close structural similarity to PPi (pyrophosphate) and high affinity to bone mineral allows bisphosphonates to achieve a high local concentration throughout the entire skeleton. Accordingly, bisphosphonates close affinity to bone mineral is a form of therapy for skeletal disorders. Intracellular accumulation of these nonhydrolyzable ATP analogues is believed to be cytotoxic to osteoclasts because they inhibit multiple ATP-dependent cellular processes, leading to osteoclast apoptosis.

Members of the second-generation bisphosphonates (pamidronate, alendronate, risedronate, zolendronate, and ibandronate) are called nitrogen-containing bisphosphonates (NCBPs). These bisphosphonates contain nitrogen at the R2 side chain, 204. The presence of a nitrogen group at the R2 position increases the anti-resorptive potency of NCBPs 10 to 10,000 times relative to first generation bisphosphonates such as disodium etidronate. However, NCBPs take up only $\frac{1}{1000}$ to $\frac{1}{10000}$ of the surface saturation capacity of hydroxyapatite. This causes the ability of NCBPs to inhibit crystallization and calcification to be much weaker than that of disodium etidronate.

Kamini™ solves several delivery and tolerability issues inherent to the bisphosphonate class while potentially increasing compliance, efficacy, and overall patient outcomes. Immediate-release etidronate disodium was reformulated into Kamini™ for the following reasons: (a) reduced side effects; (b) increased efficacy; (c) increased absorption; (d) targeted/directed delivery; (e) increased compliance through once-daily drug delivery and oral drug delivery; (f) favorable use in difficult-to-treat patient populations; (g) use in pediatric patients; (h) disease modification (epilepsy, neurodegeneration, Alzheimer's Disease, etc.); (i) use of the 505b2 drug approval pathway.

Figure 3:
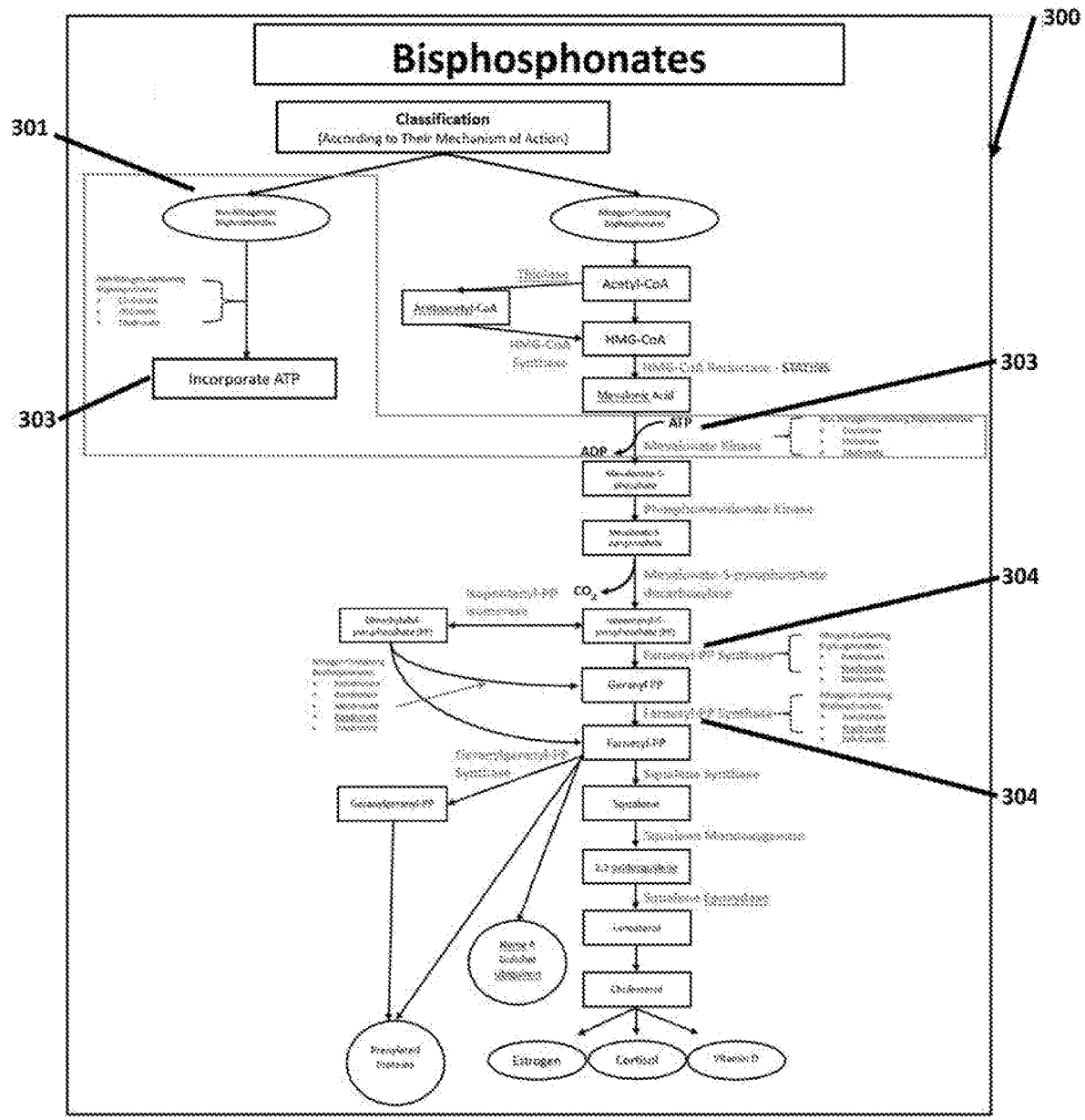
FIG. 3. Schematic Diagram of Mechanisms of Action of Two Types of Bisphosphonates.

FIG. 3 details the two accepted and separate mechanisms of action of the two types of bisphosphonates (non-nitrogen-containing bisphosphonates, nitrogen-containing bisphosphonates, 300. As detailed on the left of FIG. 3, 301, the non-nitrogen-containing bisphosphonates (etidronate, clodronate, and tiludronate) include as their mechanism of action the inhibition of bone resorption through pro-apototic effects on osteoclasts. At the molecular level, they are metabolized to toxic analogues of adenosine triphosphate, 303, which are taken up by osteoclast cells. In addition, due to their high affinity to solid-phase calcium phosphate, first-generation bisphosphonates can inhibit the formation, aggregation, and dissolution of hydroxyapatite crystals, thereby inhibiting calcification. Due to its ability to suppress calcification at high doses, disodium etidronate was used to treat ectopic calcification after spine damage and hip joint formation.

Second-generation bisphosphonates (pamidronate, alendronate, risedronate, zolendronate, and ibandronate) are referred to as nitrogen-containing bisphosphonates as they contain a nitrogen group at the R2 side chain position. At the molecular level, NCBPs inhibit the farnesyl pyrophosphate synthase step in the mevalonate pathway, 304. This modifies the isoprenylation of guanosine triphosphate-binding proteins. The process of prenylation is essential to anchor farnesylated and geranyl-geranylated GTPases in cell membranes, and loss of membrane-bound GTPases in osteoclasts is responsible for the disruption of downstream signaling pathways which promote the bone resorption process and consequently induce osteoclast apoptosis. Nitrogen-containing bisphosphonates have the capacity to cause greater osteoclast apoptosis than then first-generation non-nitrogen-containing bisphosphonates.

The introduction and widespread use of bisphosphonates into clinical practice, which occurred after the Food and Drug Administration (FDA) approval of alendronate in 1995, was largely driven by the use of this class of skeletal anti-resorptive agents to treat post-menopausal osteoporosis (PMO). Bisphosphonates have been traditionally used for diseases of the bone including: Paget's Disease, heterotopic ossification, and post-menopausal osteoporosis. As these indications were discovered and bisphosphonates were developed as treatment, pharmaceutical development programs were modified to create formulations that could be given once-weekly, once-monthly, and eventually annually. There was also a move away from first-generation to second and third-generation bisphosphonates to increase anti-resorption properties and increase the drug's half-life. However, these newer bisphosphonates are amino-bisphosphonates and work by different mechanisms than etidronate's 'bulk action' adsorption and chelation of calcific deposits (the major therapeutic target of the present invention, fully described in the claims, for the selected disease indications) rather than focusing on osteoclast inhibition for bone use.

The present invention, fully described in the claims, uses disodium etidronate, a first-generation bisphosphonate for several additional reasons. These include: etidronate does not contain nitrogen atoms: (a) long processing nitrogen; bisphosphonates containing nitrogen are more prone to causing upper GI tract ulcerations; (b) nitrogen-containing-bisphosphonates cannot be used in patients with anatomical or motility disorders of the upper gastrointestinal tract; (c) less potency (potency is related to anti-resorptive effects), non-nitrogen-containing first-generation bisphosphonates, (disodium etidronate) appear to have better upper gastrointestinal tolerability. This attribute is extremely important due to the potential young age of many of the patients who will take Kamini™: Non-nitrogen containing bisphosphonates like disodium etidronate are less likely to interfere with FPP synthase which shuts down prenylation of intracellular proteins of the mevalonic pathway (as shown in FIG. 3) that leads to apoptosis of osteoclasts, while not adversely affecting calcium chelation. First-generation bisphosphonates like disodium etidronate are metabolized to form analogues of adenosine triphosphate (ATP), which interfere with the mitochondrial adenosine diphosphate (ADP)/ATP translocase, which results in osteoclast apoptosis. While this is favorable for treating post-menopausal osteoporosis, it is not a favorable for long-term treatment of children and young adults with Neurocysticercosis, Tuber Sclerosis Complex, or Sturge-Weber Syndrome. The use of drug holidays may be adopted with the use of Kamini™ to reduce side effects cause by osteoclast apoptosis. Second-generation bisphosphonates are much greater inhibitors of osteoclasts.

The presence of a nitrogen group at the R2 position in second-generation, nitrogen-containing bisphosphonates increases the anti-resorptive potency of NCBPs 10 to 10,000 times relative to first generation bisphosphonates such as disodium etidronate. However, nitrogen-containing bisphosphonates take up only $\frac{1}{1000}$ to $\frac{1}{10000}$ of the surface saturation capacity of hydroxyapatite. This causes the ability of nitrogen-containing bisphosphonates to inhibit crystallization and calcification to be much weaker than that of disodium etidronate. Disodium etidronate is an excellent chelator of calcium, inhibits crystallization and calcification to a much greater extent than second-generation nitrogen-containing bisphosphonates, and causes less osteoclast apoptosis than second-generation bisphosphonates.

Disodium etidronate (first-generation bisphosphonate) has a much shorter half-life than 2nd and 3rd generation bisphosphonates: (a) disodium etidronate plasma's half-life=6 hours; (b) alendronate plasma's half-life=10 years: (c) zolendronic acid plasma's half-life=146 hours.

The present invention, fully described in the claims, uses a bisphosphonate that is effective but not incredibly long-acting. Daily use of these medications is preferred to weekly, monthly, or annually administered medications for compliance reasons. In case of adverse reaction, the medication can be stopped and levels of the active drug will decrease but the chelating ability of etidronate will continue.

First-generation bisphosphonates have double to quadruple the absorption percentage compared to 2nd and 3rd generation bisphosphonates. Disodium etidronate has 3% absorption that can be increased with directed delivery to the proximal jejunum using extended-release and release-modification formulations. The goal of the present invention, more fully described in the claims, is to double or triple the amount of disodium etidronate absorbed by the bowel by using the novel drug delivery model utilized by Kamini™. Increased absorption may lead to lower doses, increased efficacy, and lower incidence of side effects.

When compared to other well-known bisphosphonates (clodronate disodium, pamidronate disodium, alendronate sodium, ibandronate sodium, risedronate sodium, and zolendronate disodium), disodium etidronate has favorable pharmacokinetics, pharmacodynamics, and other drug characteristics: (a) $\Delta$E—Stabilization Energy (Presented values of stabilization energy ($\Delta$E) are negative both in water and diethyl ether medium, however, they indicate that studied compounds should be better soluble in water than in diethyl ether. Kamini™ ($\Delta$E=−850.19 kJ/mol) is highly water soluble and will therefore distribute evenly into bodily tissues.); (b) $\Delta$Gsol—Free Energy of Solvation (The $\Delta$Gsolv value is a measure of lipophilicity and indicates that bisphosphonates fall into the third class of Biopharmaceutical Classification System (BCS). Although Kamini™ ($\Delta$Gsol=−585 kJ/mol) is not highly lipid-soluble, it rivals bisphosphonates such as zolendronic acid ($\Delta$Gsol=561.99 kJ/mol). This may allow for greater movement across the Blood Brain Barrier (BBB). (c) Electrostatic potential (ranges of electrostatic potential define polarity of compounds). Wider range of electrostatic potential indicates stronger interaction of the molecule with water medium, due to increased dipole moment. The range of negative electrostatic potential distribution at isodensity surfaces of clodronate disodium salt, etidronate disodium salt, pamidronate disodium salt and zoledronate disodium salt molecules indicate a high ability to form hydrogen bonds necessary to affect the substances interaction with polar water solvent. (d) Kamini™ has an electrostatic potential range of −3679.79 to −1975.31; (e) Partition and distribution coefficients estimated by the log P and log D values. (The partition coefficient parameter describes the lipophilic properties of studied compounds. Negative values of log P indicate that they are readily soluble in water and potentially cannot diffuse across cell membranes). Similar to $\Delta$E, $\Delta$Gsolv and electrostatic potential rates, most predicted values of log P indicate that the selected compounds have an affinity for both polar and nonpolar solvent but the affinity is stronger in the case of the polar solvent. The values of log D may indicate low bioavailability which is dependent on the pH changes in the gastrointestinal tract.)

The ΔE and ΔGsolv values for studied compounds reveal that the clodronate disodium salt, etidronate disodium salt, pamidronate disodium salt and zoledronate disodium salt have a stronger affinity to water than the other bisphosphonates molecules.

Disodium etidronate has favorable hydrophilicity/lipophilicity and therefore favorable water and fat solubility characteristics that allow for (1) increased gut absorption (2) potentially increased crossing of semi-permeable membranes especially the blood brain barrier.

The manufacture of Kamini™ using GMP but in addition in conformance with 21 CFR211 C (g) incorporates secure and flexible architecture for blockchain technology for visibility, verification, and validation.

Figure 4:
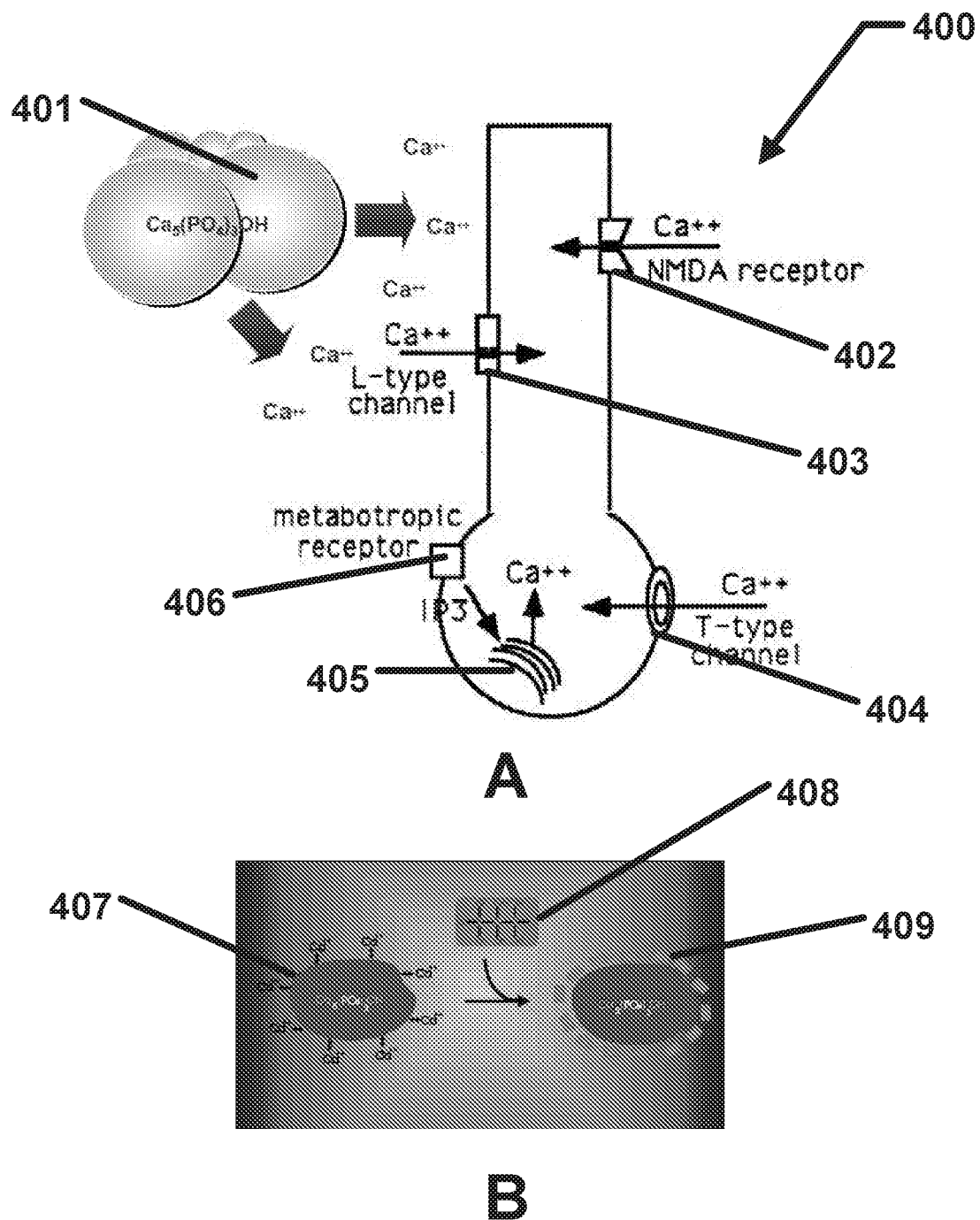
FIG. 4. Schematic Diagram of Kamini™ Therapeutic Interaction.

FIG. 4 show schematic diagram, 400, of presumed action of Kamini™ against the damaging effects of excess Calcium ions on neurons. In FIG. 4A a high concentration of Calcium ions produced by calcium deposits, 401, can enter a neuron through the NMDA receptor, 402, through the L-channel, 403, through the T-channel, 404, or be released from internal calcium stores in the endoplasmic reticulum, 405, by activation of a metabotropic receptor, 406. Excess internal calcium ions can trigger neuronal firing that can serve as an epileptic foci or kill the neuron. Disodium etidronate acts on bone through a high affinity interaction with hydroxyapatite. As illustrated in FIG. 4B, in vitro, disodium etidronate, 408, has a high affinity for solid-phase calcium phosphate, 407, and thereby inhibits both the formation and dissolution of hydroxyapatite. In solution, disodium etidronate inhibits the precipitation of calcium phosphate, blocks the transformation of amorphous calcium phosphate into hydroxyapatite, and delays aggregation of apatite crystals into larger clusters which can lead to calcinosis. It also works by inhibiting the formation, growth, and dissolution of hydroxyapatite crystals and their amorphous precursors by chemisorption to calcium phosphate surfaces, 409. Inhibition of crystal resorption occurs at lower doses than are required to inhibit crystal growth. Both effects increase as the dose increases.

Disodium etidronate is not metabolized. The amount of drug absorbed after an oral dose is approximately 3%. In normal subjects, plasma half-life (t½) of disodium etidronate, based on non-compartmental pharmacokinetics is 1 to 6 hours. Within 24 hours, approximately half the absorbed dose is excreted in urine; the remainder is distributed to bone compartments from which it is slowly eliminated. Animal studies have yielded bone clearance estimates up to 165 days. In humans, the residence time on bone is postulated to be due to such factors as specific metabolic condition and bone type. Unabsorbed drug is excreted intact in the feces.

Due to the structural similarity of brain stones to the hydroxyapatite structure inherent to bone, it is postulated that by binding to their surface etidronate produces a stable structure less likely to release toxic levels of calcium into the intracellular space leading to seizures, headaches, and other neurologic disorders related to calcinosis. A schematic showing this mechanism of action is shown. In fact, Loeb found that disodium etidronate does not reduce the size of intracerebral calcifications. Seizure and headache reduction ability was therefore attributed to disodium etidronate's ability to reduce the amount of freely circulating calcium ions ($Ca^{++}$). It has also been postulated that treatment early in the disease process will prevent or reduce further growth of calcific brain deposits thereby slowing or stopping disease progression. This has disease-modifying implications if the patient is treated early enough in the progression of the disease. The present invention, fully described in the claims, with early treatment of intracranial calcification can slow or even prevent the neurodegenerative process.

The present invention, fully described in the claims, for calcium chelation using Kamini™, a modified-delivery version of the bisphosphonate bone drug disodium etidronate can improve these symptoms and lead to better outcomes for patients. Further, directed delivery of Kamini™ into the proximal jejunum of the small intestine using modern pharmaceutical dosing formulations will improve its efficacy and patient compliance while simultaneously reducing debilitating side effects that historically limited the original medication's use.

There is a desperate need for disease-modifying therapeutics with novel mechanisms of action. The effective use of the non-modified, immediate-release versions of disodium etidronate in the parkinsonian features of a patient with extensive basal ganglia calcifications due to Fahr's Disease as well as a reduction in seizures and headaches in other patients with brain calcifications, provide important clinical data to support developing Kamini™. The present invention, fully described in the claims, targets Orphan Disease indications, including Neurocysticercosis, Tuberous Sclerosis Complex, and Sturge-Weber Syndrome. The present invention, fully described in the claims, builds upon these clinical findings with novel data demonstrating that treatment of brain calcifications with Kamini™ has a disease-modifying, positive effect on these and potentially other neurological diseases. This approach is highly complementary to existing therapies and represents an entirely new 'disease-modifying' approach that has the potential for more widespread usage. Kamini™ (disodium etidronate extended release) works by: (a) preventing calcium phosphate breakdown; (b) inhibiting the precipitation of calcium phosphate; (c) blocking the transformation of amorphous calcium phosphate into hydroxyapatite; (d) and delaying aggregation of apatite crystals into larger clusters.

Kamini™ can reach brain calcifications through break down of the blood brain barrier, a common feature in calcinosis. Once there, the drug may bind calcifications with high affinity, protecting neurons from toxic calcium levels that promote excitability and death.

Figure 5:
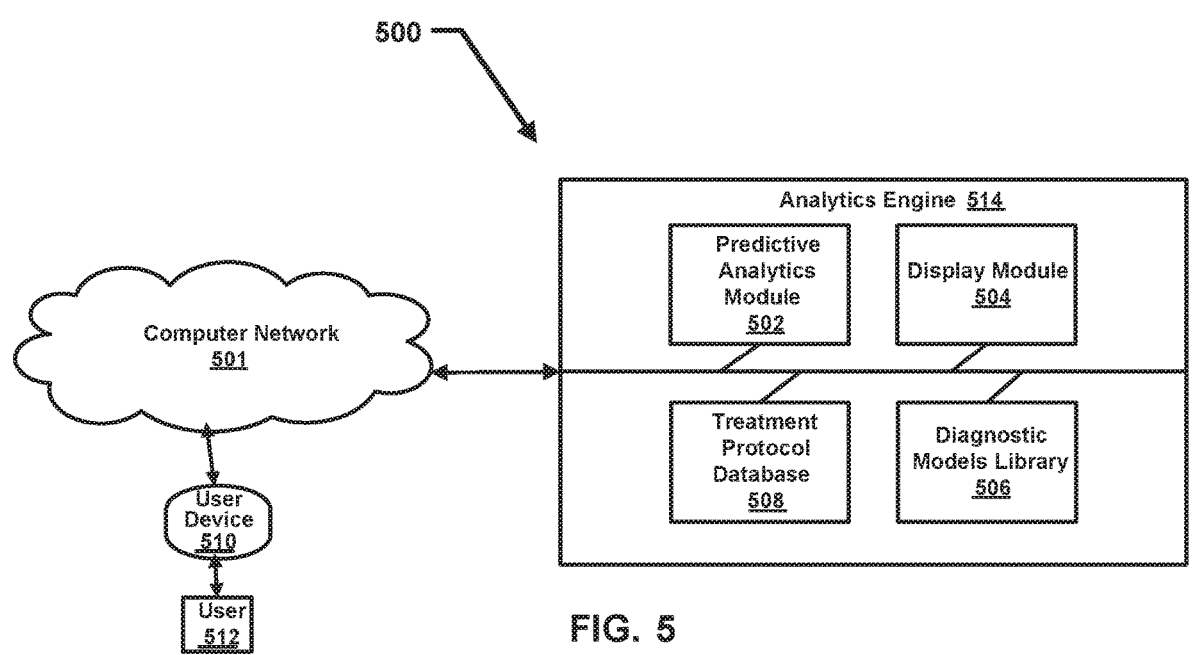
FIG. 5. Computer Block Diagram of Healthcare Analytic Engine.

In FIG. 5 is shown a computer-implement functional block diagram, 500, of the medical intelligence system for treating calcinosis conditions, such as Neurocysticercosis, Tuberous Sclerosis Complex, and Sturge-Weber Syndrome, Neurocysticercosis. A User, 512, makes an enquiry through a User Device, 510, to the Analytics Engine, 514, which comprises several components is connected to a computer network, 501, and includes a Predictive Analytics Module, 502, using among other features the Diagnostics Models Library, 508, to operate on the Treatment Protocol Database, 506, to determine from historical data and current observations of a patient, the optimal treatment, for the calcinosis condition. Instructions, diagrams, and protocols can be communicated to the User, 512, by means of the User Device, 510, or Display Module, 504.

Figure 6:
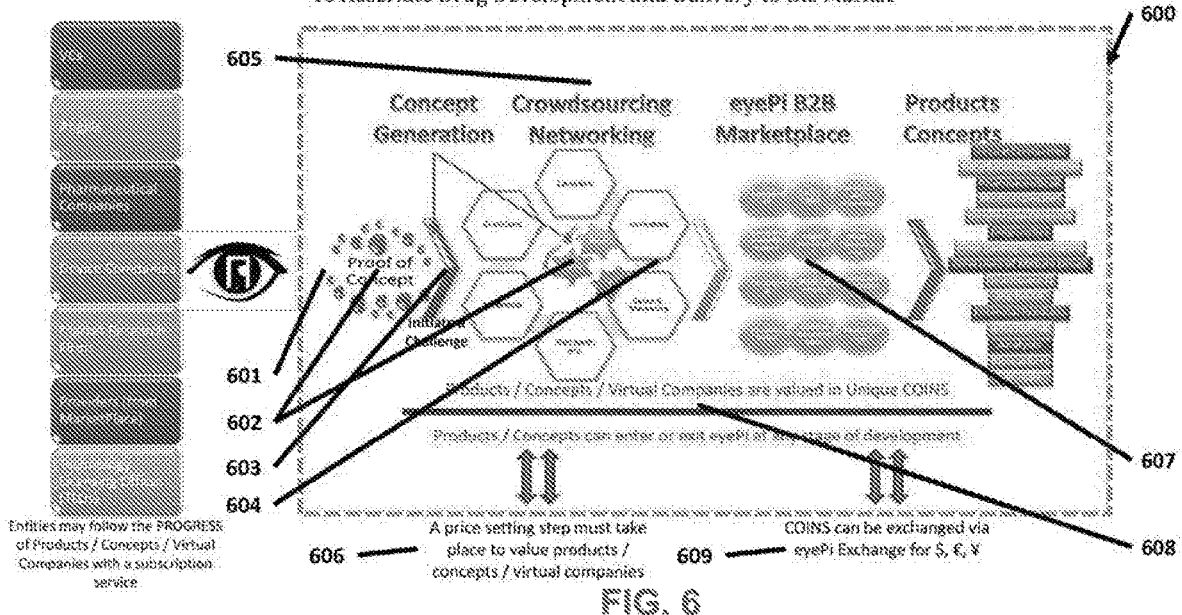
FIG. 6. Schematic Diagram of the Application of Blockchain Technology.

The use of Blockchain technology empowers all people to create and innovate by providing them with Capital, Expertise, and Resources. Blockchain technology is an open, distributed, and immutable ledger that can record transactions between two or more parties efficiently and in a verifiable and pertinent way. Blockchain Technology also allows for the assignment of micro-values to data at particular times, thus allowing for sustainable ownership of ideas and assignment of rights to property including intellectual property, digital assets and stocks, records, identity, cryptoequities/cryptosecurities, idea futures/idea markets, and other digital and real products. The use of blockchain technology, shown in FIG. 6 to foster drug development can be detailed with the following process, 600: 1) conceptualization, 601, a) ideas/needs from outside the marketplace/exchange; b) ideas/needs organically derived by the marketplace/exchange/network; 2) creation of the idea/concept, 602, a) administrators and network help frame the idea; 3) challenge the network with questions (quests/challenges), 603, a) administrators and network help users/contributors ask the right questions and frame those questions; 4) refinement of the idea/concept, 604, a) crowdsourcing with expert network; 5) validation of the concept, 605; 6) medical innovation futures market, 606, a) ideas futures/ideas markets (ideas marketplace), b) cryptosecurities/cryptoequities, and c) ideas brokerage (based on cryptocurrencies); 7) skills exchange/internal B2B marketplace, 607: a) brokering of resources and b) brokering of services; 8) tokenization of ideas, products, companies, 608: a) brokering of funding and b) creation of COINS to fund ideas, concepts, products, companies; 9) cryptoequities exchange, 609: a) ability to trade virtual companies (COINS) on the exchange, b) ability to convert tokens/COINS into physical fiat currency, c) clearing mechanism to value ideas, concepts, products, companies and sell them to the outside world. The entire drug development process can be placed into the blockchain (full transparency), 1) drug provenance—tracking of drug to eliminate drug diversion and counterfeit; 2) use of the blockchain to perform due diligence in business development and licensing decisions, a) due diligence teams in pharmaceutical/biotech companies are usually comprised of no more than 4 to 6 individuals to assess the validity of all business development and licensing opportunities for the company in a given year. This is an impossible task and many excellent partnering opportunities are missed. The use of blockchain technology and smart contracts would allow distributed teams to assess the value of potential business development and licensing opportunities without giving away plans and compromising potential intellectual property. Smart contracts also allow companies to ensure basic questions about deals are answered. For example, smart contracts a) allow for business between micro-businesses and entities; in the past, only large companies had the resources necessary to perform a true due diligence analysis. Due diligence can now be performed utilizing smart contract technology and go/no go decision trees of two types: a) scientific due diligence and b) business due diligence. Smart contracts can be used for yes/no—go/no go decisions regarding treatment protocols; a) valuation of individual projects and/or proofs of concept (tokenization); b) trading of pre-IPO securities related to developmental ideas/concepts related to developmental ideas/proofs of concepts; c) management of overall clinical drug development processes and timelines; 4) blockchain-based smart contract management of process, timelines, and milestones (i.e., smart contract that only pays out when a clinical trial site randomizes the pre-determined number of study subjects); 5) drug development milestones and GANNT/Go—No Go decision making process; 6) intellectual property/proportional ownership of intellectual property based on proof of work and amount of actual work performed on a given project (meritocracy); 7) blockchain-based management of clinical trial protocols; 8) blockchain-based clinical trial management: a) clinical trial data and comments from investigators/regulators; b) clinical trial outcomes reported directly by study patients; c) tracking of study drug/finished product (per new FDA guidance at https://www.accessdata.fda.gov/scripts/cdrh/cfdocs/cfcfr/CFR.Search.cfm?CFRPart=211&showFR=1&subpartNode=21:4.0.1.1.11.7).

Figure 7:
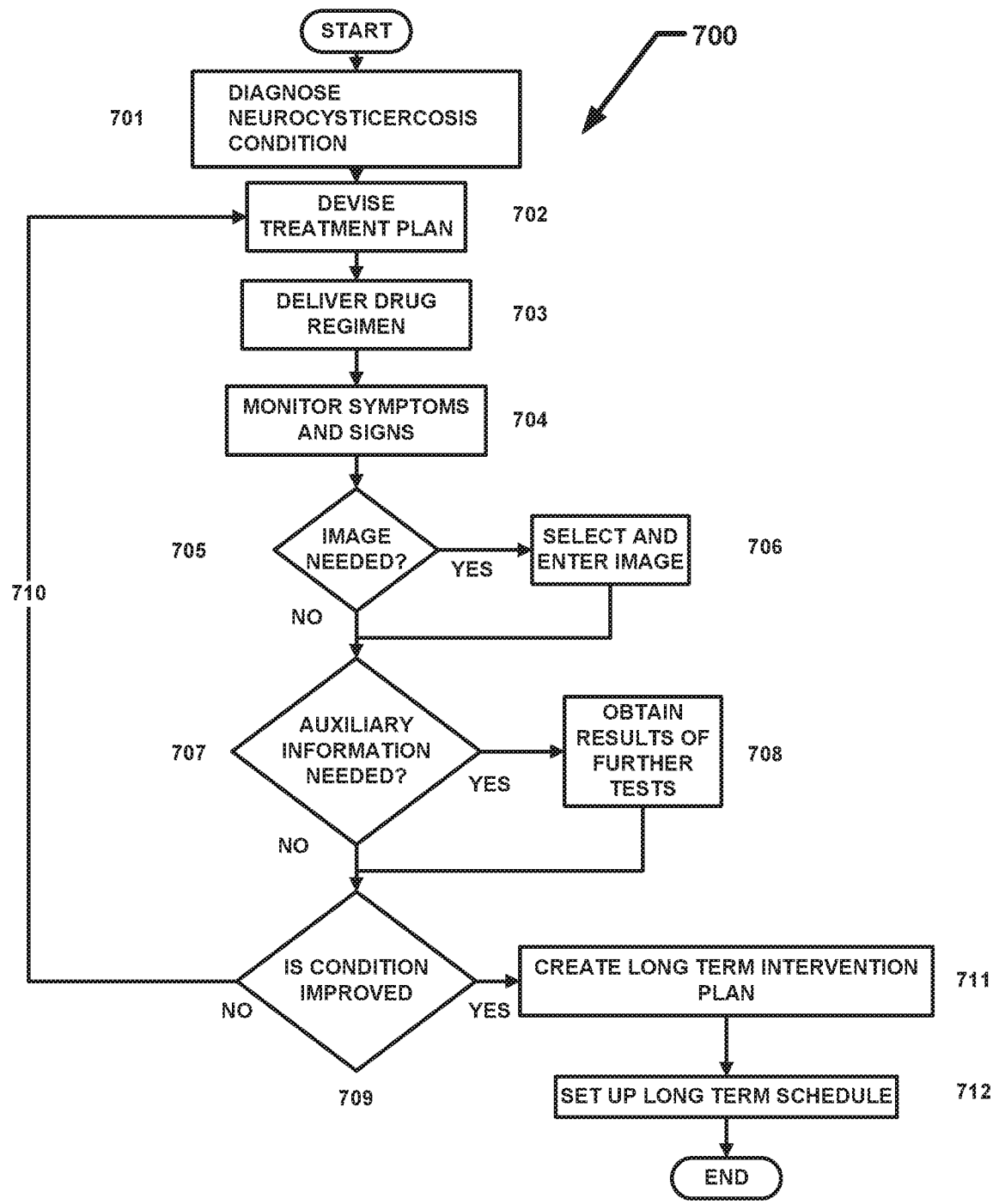
FIG. 7. Flowchart of Diagnosis and Treatment of Neurocysticercosis.

FIG. 7 shows a Flow Chart, 700, for the method of treating Neurocysticercosis, which employs blockchain technology for clinical drug delivery (drug provenance) and patient tracking. Using among other means the medical intelligence system, 500, the patient's condition is diagnosed, 701, and a suitable treatment plan devised, 702. Then following the delivery drug regimen, 703, a safe and effective amount of the pharmaceutical composition, Kamini™, is provided, comprising a bolus of disodium etidronate, a bisphosphonate in oral dosage form designed with an enteric coating for delayed release and pharmaceutically effective absorption in the gastrointestinal tract beyond the small intestine in the large intestine using a chelating agent. Neurological symptoms and signs are monitored, 704, which may require, 705, obtaining additional information such as MRI images, 706, or which may require other auxiliary information, 707, including obtaining results of further tests, 708. One such test would determine the concentration of the drug in the patient's spinal fluid to ensure that the drug is present at a therapeutic level. The patient's condition will be monitored for improvement, 709. If there is no improvement, 710, then the unit dosage or other aspects can be modified. If the patient's condition has improved then using the medical intelligence system, 500, a long-term treatment plan can be devised, 711, and implemented, 712.

In determining the drug regimen, 703, Neurocysticercosis can present at any age. However, if Kamini™ is formulated as extended-release oral capsules as well as extended release chewable tablets and extended release liquids then it can be presented to patients who by age or disability have difficulty swallowing large capsules so deterioration of their neurological condition can be prevented.

The advantages of targeted/direct delivery of Kamini™ to the Proximal Jejunum are several: (a) increased, absorption=increased efficacy (immediate-release is only 3% absorbed); (b) decreased side effects (esophageal, stomach, and duodenal ulcers/issues with Barret's Esophagus); (c) increased compliance for patients/ease of administration; and (d) greater dose variability for pediatric patients.

Such formulations offer convenience, functionality and so provide the capability of successfully treating pediatric patients who normally would not be able to swallow large, enteric-coated tablets/capsules. There are currently no disease-modifying drugs for epilepsy. Reformulated Kamini™ with easily administered enteric-coated etidronate can be disease modifying if used early in the epileptogenic process. Additionally, there is the potential for companion diagnostics.

With monitoring the patient's neurological symptoms and signs, 704, along with additional image information, 706, from measurements and tests, 708, the criterion for improvement of the patient's condition are at a minimum a 50% reduction in epileptic seizure frequency over a 28-day period from baseline to maintenance with a 50% responder rate. In addition, a 50% reduction in headache frequency per 28 days from baseline to the maintenance period along with increased headache relief scores and total pain relief (TOT-PAR).

Figure 8:
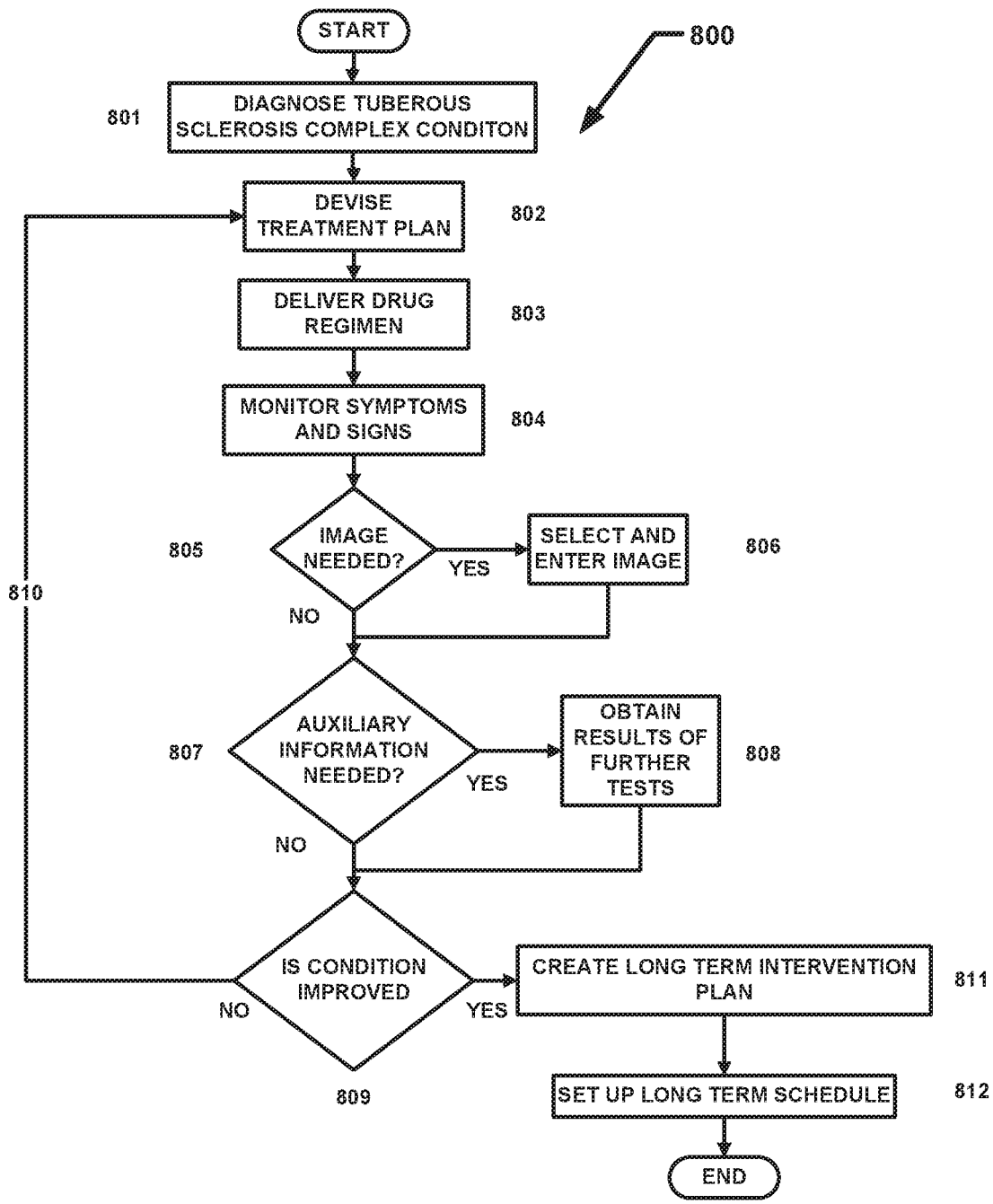
FIG. 8. Flowchart of Diagnosis and Treatment of Tuberous Sclerosis Complex.

FIG. 8 shows a Flow Chart, 800, for the method of treating Tuberous Sclerosis Complex, which employs blockchain technology for clinical drug delivery (drug provenance) and patient tracking. Using among other means the medical intelligence system, 500, the patient's condition is diagnosed, 801, and a suitable treatment plan devised, 802.

Then following the delivery drug regimen, 803, which uses a safe and effective amount of the pharmaceutical composition, Kamini™, comprising a bolus of disodium etidronate, a bisphosphonate in oral dosage form designed with an enteric coating for delayed release and pharmaceutically effective absorption in the gastrointestinal tract beyond the small intestine in the large intestine using a chelating agent. neurological symptoms and signs are monitored, 804, which may require, 805, obtaining additional information, such as MRI images, 806, or which may require other auxiliary information, 807, include obtaining results of further tests, 808. One such test would determine the concentration of the drug in the patient's spinal fluid to ensure that the drug is present at a therapeutic level. The patient's condition will be monitored for improvement, 809. If there is no improvement, 810, then the unit dosage or other aspects can be modified. If the patient's condition has improved then using the medical intelligence system, 500, a long-term treatment plan can be devised, 811, and implemented, 812.

In determining the Drug Regimen, 803, Tuberous Sclerosis Complex can present in young children so Kamini™ is formulated as extended-release oral capsules as well as extended release chewable tablets and extended release liquids. Many of these patients could be as young as 1 to 2 years of age at onset of disease and have progressive neurological deterioration that at present time is not preventable. Similar formulations would accommodate patients with difficulty swallowing.

The advantages of targeted/direct delivery of Kamini™ to the proximal jejunum are several: (a) increased absorption=increased efficacy (immediate-release is only 3% absorbed); (b) decreased side effects (esophageal, stomach, and duodenal ulcers/issues with Barret's Esophagus); (c) increased compliance for patients/ease of administration; and (d) greater dose variability for pediatric patients.

Such formulations offer convenience, functionality and so provide the capability of successfully treating pediatric patients who normally would not be able to swallow large, enteric-coated tablets/capsules. There are There are currently no disease modifying drugs for epilepsy. Reformulated. Kamini™ with easily administered enteric-coated etidronate can be disease modifying if used early in the epileptogenic process. Additionally, there is the potential for companion diagnostics.

With monitoring the patient's neurological symptoms and signs, 804, along with additional image information, 806, from measurements and tests, 808, the criterion for improvement of the patient's condition are at a minimum a 50% reduction in epileptic seizure frequency over a 28-day period from baseline to maintenance with a 50% responder rate. In addition, a 50% reduction in headache frequency per 28 days from baseline to the maintenance period along with increased headache relief scores and total pain relief (TOT-PAR).

Figure 9:
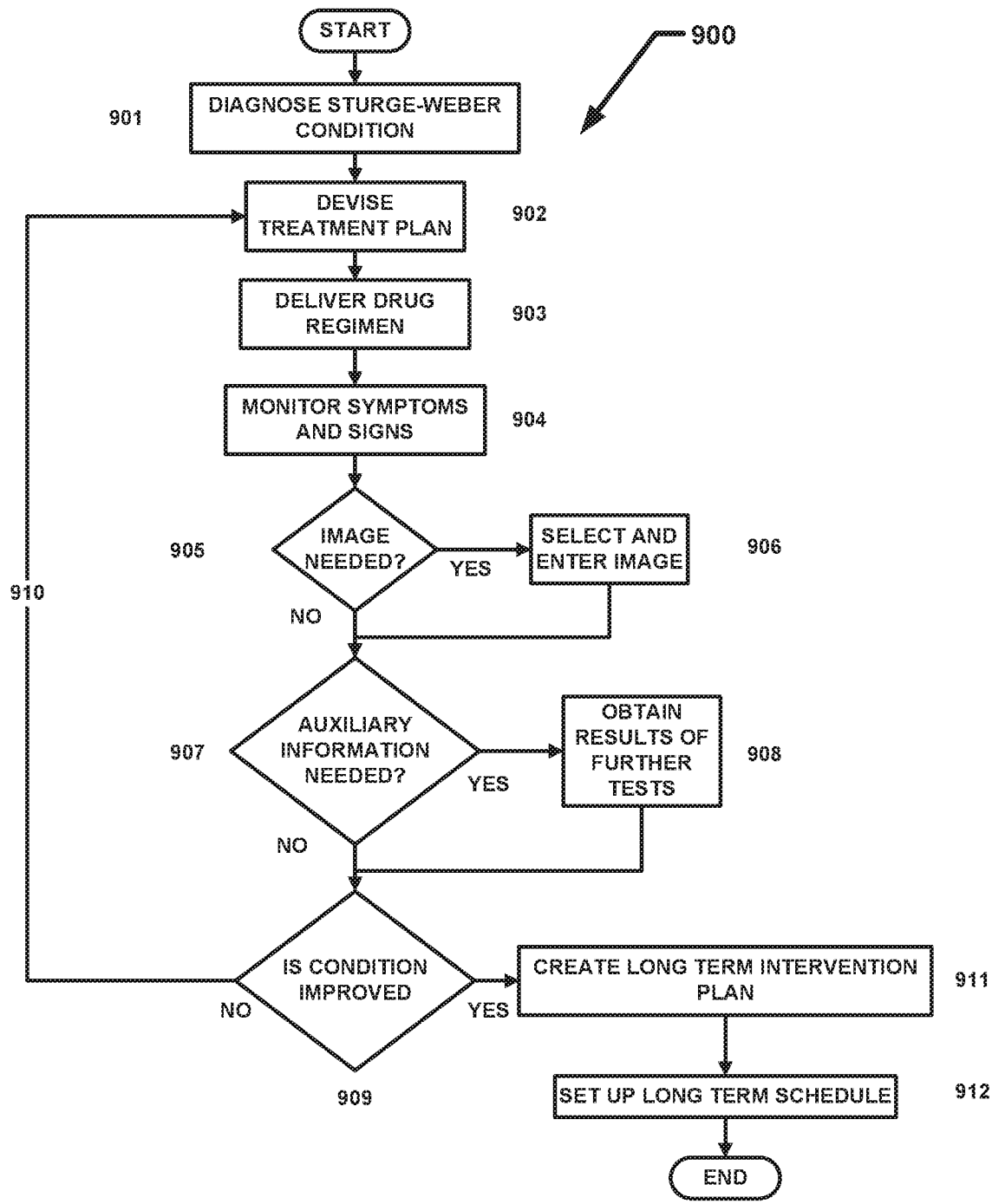
FIG. 9. Flowchart of Diagnosis and Treatment of Sturge-Weber Syndrome.

FIG. 9 shows a Flow Chart, 900, for the method of treating Sturge-Weber Syndrome, which employs blockchain technology for clinical drug delivery and patient tracking. Using among other means the medical intelligence system, 500, the patient's condition is diagnosed, 901, and a suitable treatment plan devised, 902. Then following the delivery drug regimen, 903, which includes a safe and effective amount of the pharmaceutical composition, Kamini™, comprising a bolus of disodium etidronate, a bisphosphonate in oral dosage form designed with an enteric coating for delayed release and pharmaceutically effective absorption in the gastrointestinal tract beyond the small intestine in the large intestine using a chelating agent. Neurological symptoms and signs are monitored, 904, which may require, 905, obtaining additional information, such as MRI images, 906, or which may require other auxiliary information, 907, such as obtaining results of further tests, 908. One such test would determine the concentration of the drug in the patient's spinal fluid to ensure that the drug is present at a therapeutic level. The patient's condition will be monitored for improvement, 909. If there is no improvement, 910, then the unit dosage or other aspects can be modified. If the patient's condition has improved then using the medical intelligence system, 500, a long-term treatment plan can be devised, 911, and implemented, 912.

In determining the drug regimen, 903, Sturge-Weber can present in young children, so Kamini™ has been formulated as an extended-release oral capsules as well as extended release chewable tablets and extended release liquids. Many of these patients could be as young as 1 to 2 years of age at onset of disease and have progressive neurological deterioration that at the present time are not preventable. Similar formulations would accommodate patients with difficulty swallowing.

The advantages of targeted/direct delivery of Kamini™ to the proximal jejunum are several: (a) increased absorption=increased efficacy (immediate-release is only 3% absorbed); (b) decreased side effects (esophageal, stomach, and duodenal ulcers/issues with Barret's Esophagus); (c) increased compliance for patients/ease of administration; and (d) greater dose variability for pediatric patients.

Such formulations offer convenience, functionality and so provide the capability of successfully treating pediatric patients who normally would not be able to swallow large, enteric-coated tablets/capsules. There are currently no disease-modifying drugs for epilepsy. Reformulated Kamini™ with easily administered enteric-coated etidronate can be disease modifying if used early in the epileptogenic process. Additionally, there is the potential for companion diagnostics.

With monitoring the patient's neurological symptoms and signs, 904, along with additional image information, 906, from measurements and tests, 908, the criterion for improvement of the patient's condition are at a minimum a 50% reduction in epileptic seizure frequency over 28 days from baseline to maintenance with a 50% responder rate. In addition, a 50% reduction in headache frequency per 28 days from baseline to the maintenance period along with increased headache relief scores and total pain relief (TOT-PAR).

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

While the invention has been described by reference to certain preferred embodiments, it should be understood that these embodiments are within the spirit and scope of the inventive concepts described. Accordingly, it is intended that the invention not be limited by the embodiments, but that it have the full scope permitted by the language of the following claims.

It will be apparent that the precise details of the methods or compositions described herein may be varied or modified without departing from the spirit of the described invention. The applicants claim all such modifications and variations that fall within the scope of the claims below.

The embodiments of the invention in which an exclusive property or privilege is claimed are defined as follows:

1. A method for using disodium etidronate for preventing the development of calcifications that could led to neurological symptoms in human patients lacking calcifications, taken from a patient population diagnosed with a condition taken the group consisting of Sturge-Weber Syndrome, Tuber Sclerosis Complex, and Neurocysticercosis, the method comprising:
   (a) diagnosing Sturge-Weber Syndrome by means comprising at least one of radiological imaging of leptomeningeal angiomas in the brain, symptom history of Port Wine Birthmark, ocular glaucoma, or tissue genetic testing for GNAQ somatic mutation;
   (b) diagnosing Tuber Sclerosis Complex by means comprising at least one of radiological imaging of cortical tubers, subependymal nodules, symptom history of autism spectrum disorder, or genetic testing for gene TSC1 and TSC2 mutations;
   (c) diagnosing Neurocysticercosis by means comprising at least one of radiological imaging of cystic brain lesions, positive serology for taenia solium, or travel or living history in endemic regions;
   (d) administrating a calcinosis-preventing drug regimen comprising disodium etidronate once or twice daily at a dosage of 2.5 to 20 mg/kg/per day to the diagnosed patients;
   (e) monitoring the amount of calcinosis by means of radiological imaging;
   (f) obtaining auxiliary medical information of the level of calcinosis by means of symptoms presentation, said symptoms comprising headache, epileptic seizures, behavioral disturbance;
   (g) and modifying said calcinosis-preventing drug regimen to ameliorate side effects by means comprising dosage adjustment, drug holiday periods.

* * * * *